US012416045B2

(12) United States Patent
Gradia

(10) Patent No.: US 12,416,045 B2
(45) Date of Patent: Sep. 16, 2025

(54) METHOD OF CAPTURING CRISPR ENDONUCLEASE CLEAVAGE PRODUCTS

(71) Applicant: Caribou Biosciences, Inc., Berkeley, CA (US)

(72) Inventor: Scott David Gradia, Albany, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 0 days.

(21) Appl. No.: 18/715,913

(22) PCT Filed: Dec. 5, 2022

(86) PCT No.: PCT/US2022/080938
§ 371 (c)(1),
(2) Date: Jun. 3, 2024

(87) PCT Pub. No.: WO2023/107899
PCT Pub. Date: Jun. 15, 2023

(65) Prior Publication Data
US 2025/0034633 A1    Jan. 30, 2025

Related U.S. Application Data

(60) Provisional application No. 63/286,922, filed on Dec. 7, 2021.

(51) Int. Cl.
*C12Q 1/6855* (2018.01)

(52) U.S. Cl.
CPC .................... *C12Q 1/6855* (2013.01)

(58) Field of Classification Search
CPC ............ C12Q 1/6855; C12Q 2521/301; C12Q 2521/319; C12Q 2525/191; C12Q 2531/113; C12Q 2563/179
See application file for complete search history.

(56) References Cited

U.S. PATENT DOCUMENTS

| 9,650,617 | B2 * | 5/2017 | May | ........................ C12N 9/16 |
| 2004/0209299 | A1 | 10/2004 | Pinter et al. | |
| 2019/0211374 | A1 | 7/2019 | Makarov et al. | |
| 2020/0056191 | A1 | 2/2020 | Chaikind et al. | |
| 2020/0208208 | A1 | 7/2020 | George et al. | |

FOREIGN PATENT DOCUMENTS

WO    WO-2020120711 A1 *  6/2020  ........... C12Q 1/6806

OTHER PUBLICATIONS

Aslanidis et al. Minimal Length Requirement of the Single-stranded Tails for Ligation-independent Cloning (LIC) of PCR Products. PCR Methods and Applications 1994; 4: 172-177 (Year: 1994).*
Park et al. Improvement of the 3'-5' Exonuclease Activity of Taq DNA Polymerase by Protein Engineering in the Active Site. Molecules and Cells 1997; 7: 419-424 (Year: 1997).*
Stoineva et al. Enzymic Synthesis Design and Enzymic Synthesis of Aspartame. Tetrahedron 1992; 48: 1115-1122 (Year: 1992).*
Sundaresan et al. RNA-Independent DNA Cleavage Activities of Cas9 and Cas12a. Cell Reports 2017; 21: 3728-3739 (Year: 2017).*
Swartjes et al. Editor's Cut: DNA cleavage by CRISPR RNA-guided nucleases Cas9 and Cas12a. Biochemical Society Transactions 2019; 48: 207-219 (Year: 2019).*
Kartje et al. Chimeric Guides Probe and Enhance Cas9 Biochemical Activity. Biochemistry 2018; 57: 3027-3031 (Year: 2018).*
Aslanidis, C. and de Jong, P., (1990) Ligation-independent cloning of PCR products (LIC-PCR), Nucleic Acids Res. 18:6069-6074.
Cameron, P., et al.,. (2017). Mapping the genomic landscape of CRISPR-Cas9 cleavage. Nature methods, 14(6), pp. 600-606 + Online Methods section.
Christian M et al., (2010) Targeting DNA double-strand breaks with TAL effector nucleases, Genetics. 186 (2): 757-761.
Gibson, D.G., et al., (2009) Enzymatic assembly of DNA molecules up to several hundred kilobases, Nat. Methods 6, 343-345.
Gibson, D.G., et al., (2010) Creation of a Bacterial Cell Controlled by a Chemically Synthesized Genome, Science 329, 52-56.
Gilpatrick et al., (2020) Targeted nanopore sequencing with Cas9-guided adaptor ligation, Nat. Biotechnol. 38:433.
Guilinger, J. P., et al., (2014). Fusion of catalytically inactive Cas9 to FokI nuclease improves the specificity of genome modification, Nature biotechnology, 32(6), 577-582.
Kim Y.G., et al., (1996). Hybrid restriction enzymes: zinc finger fusions to Fok I cleavage domain, Proc Natl. Acad. Sci USA. 93(3): 1156-1160.
Hardigan et al. "CRISPR/Cas9-targeted removal of unwanted sequences from small-RNA sequencing libraries" Nucleic Acids Research 47(14): e84 2019.
Mikhailov, V.S. et al., Affinity Capture of Specific DNA Fragments with the Use of Short Synthetic Sequences, Bioorganicheskaya khimiya, 2013, v. 39, N. 1, p. 81-86, abstract.

* cited by examiner

*Primary Examiner* — Angela M. Bertagna
(74) *Attorney, Agent, or Firm* — Olga Zimmerman; Barbara G. McClung

(57) ABSTRACT

The invention is a method of capturing DNA ends formed by endonuclease cleavage, such as CRISPR endonuclease cleavage, for downstream analysis including amplification and sequencing.

13 Claims, 7 Drawing Sheets

Specification includes a Sequence Listing.

METHOD OF CAPTURING CRISPR ENDONUCLEASE CLEAVAGE PRODUCTS

FIELD OF THE INVENTION

The invention related to the field of nucleic acids and endonuclease-related methods, and more specifically, to the methods of capturing nucleic acids for downstream analysis such as sequencing.

STATEMENT REGARDING FEDERALLY SPONSORED RESEARCH

None.

SEQUENCE LISTING

The instant application contains a Sequence Listing which has been submitted electronically in XML format and is hereby incorporated by reference in its entirety. Said XML copy, created on Apr. 4, 2025, is named CBI043_10_SL.xml and is 40,805 bytes in size.

BACKGROUND OF THE INVENTION

Capture of nucleic acids by cloning vectors or adaptors relies on ligation. More efficient ligation involves compatible cohesive ends of nucleic acids to be ligated, i.e., the nucleic acids have overhangs capable of hybridizing to the overhangs of the ligation partner. The cohesive end ligation is more kinetically advantaged than the ligation of blunt ends where the ligation partners do not form any hybrids prior to ligation. For this reason, a popular ligation method involves creating of one-base cohesive ends via dA-tailing. Enzymatic or chemical means are employed to add a dA overhang on one ligation and a dT overhang on the other ligation partner. The dA-tailing or TA cloning are used in cloning and sequencing library formation.

While the dA-tailing method is favored because of its simplicity, the method has several disadvantages. First, an inserted A nucleotide is unwanted if the captured sequence is a coding sequence or a part of a coding sequence. Second, the dA-tailing capture is nonspecific. All nucleic acids in the sample having an accessible 3'-end will be modified by a terminal transferase to receive the 3'-terminal A, and thereby both desired and undesired nucleic acids will become substrates for the ligation reaction.

There is a need for a precise and efficient method of capturing nucleic acids cleaved by endonucleases such as restriction endonucleases and CRISPR endonucleases.

SUMMARY OF THE INVENTION

The instant invention provides a method of capturing endonuclease-cleaved nucleic acid ends by generating a 5'-overhang via controlled exonuclease digestion so that an adaptor with a 5'-overhang could be efficiently ligated. The method is an alternative to the dA-tailing method that is more efficient and more specific.

In some embodiments, the invention is a method of capturing a nucleic acid from a sample comprising a target nucleic acid and non-target nucleic acids, the method comprising: contacting a double-stranded target nucleic acid having a 3'-end with a catalyst possessing 3'-5'-exonuclease activity thereby generating a first 5'-overhang at a first 5'-end and a first recessed 3'-end in the target nucleic acid; contacting the nucleic acid with an adaptor having a second 5'-overhang at a second 5'-end, the second 5'-overhang capable of hybridizing to the first 5'-overhang thereby forming a hybrid between the first and second 5'-overhangs; and linking at least one of the first 3'-end with the second 5'-end thereby capturing the target nucleic acid by forming an adapted nucleic acid. In some embodiments, the adaptor further comprises a second recessed 3'-end, and the linking further comprises linking the first 5'-end with the second 3'-end. In some embodiments, the 3'-end of the double-stranded target nucleic acid is a part of a blunt end. In some embodiments, the 3'-end of the double-stranded target nucleic acid is a part of a 3'-overhang. In some embodiments, the 3'-end of the double-stranded target nucleic acid is generated by cleavage of the nucleic acid with a sequence-specific endonuclease.

In some embodiments, the sequence-specific endonuclease is a restriction endonuclease. In some embodiments, the sequence-specific endonuclease is a CRISPR endonuclease. In some embodiments, the sequence-specific endonuclease is a catalytically inactive CRISPR endonuclease fused to Fok I. In some embodiments, the sequence-specific endonuclease is a transcription activator-like effector nuclease (TALEN), or a TALEN-Fok I fusion. In some embodiments, the sequence-specific endonuclease is a zinc finger nuclease (ZFN), or a ZFN-Fok I fusion. In some embodiments, the catalyst possessing a 3'-5' exonuclease activity is a DNA polymerase.

In some embodiments, the DNA polymerase possessing a 3'-5' exonuclease activity is a Family A polymerase, a Family B polymerase or a Family C polymerase having the Exo I, Exo II and Exo III domains of the Klenow fragment of the $E.\ coli$ Pol I. In some embodiments, the DNA polymerase has aspartame residues corresponding to the residues D355, D424 and D501 of the Klenow fragment of $E.\ coli$ Pol I. In some embodiments, the DNA polymerase is selected from a group consisting of T4 DNA polymerase, RB69 DNA polymerase, Klenow fragment, T7 DNA polymerase, $E.\ coli$ Pol III delta fragment, eukaryotic pol epsilon, eukaryotic pol delta, and mitochondrial pol gamma.

In some embodiments, the 3'-5' exonuclease activity is exhibited in the presence of fewer than four of the dATP, dCTP, dGTP and dTTP and the contacting is with fewer than four of the dATP, dCTP, dGTP and dTTP and the 3'-5' exonuclease activity stops at the nucleotide identical to one of the fewer than four dATP, dCTP, dGTP and dTTP. In some embodiments, a single dNTP is used and the 3'-5' exonuclease activity stops at the nucleotide identical to the single dNTP.

In some embodiments, the 5'-overhang is 2-15 nucleotides long. In some embodiments, the adaptor comprises at least one of the nucleic acid barcode, a sequencing primer binding site and an amplification primer binding site. In some embodiments, the barcode is selected from a unique molecular ID (UMI) and a sample ID (SID) or both.

In some embodiments, the adaptor is formed by annealing of two nucleic acid strands. In some embodiments, the adaptor is formed by exonuclease digestion of the 3'-end to generate the oligonucleotide with the 5'-overhang. In some embodiments, the adaptor comprises a nucleic acid modification increasing the melting temperature of a nucleic acid duplex that includes the modification. In some embodiments, the adaptor comprises a sequence selected from SEQ ID NOs: 7-11.

In some embodiments, the linking is by ligation and is preceded by phosphorylating the nucleic acids or the adaptor, i.e., with a polynucleotide kinase.

In some embodiments, the method further comprises amplifying the captured nucleic acid, e.g., with an amplification primer annealing to a primer binding site in the adaptor. In some embodiments, the amplification primer comprises a sequence selected from SEQ ID NOs: 12-16. In some embodiments, the amplification is linear amplification. In some embodiments, the amplification is exponential amplification by PCR, e.g., including 5, 10, 20, 30 or 40 cycles.

In some embodiments, the adaptor is linked to a capture moiety, and the method further comprises capturing the capture moiety in the adapted nucleic acid thereby capturing the nucleic acid. In some embodiments, the capture moiety is selected from biotin, an antigen capable of binding to a capture antibody, and a capture sequence capable of hybridizing to a capture nucleic acid.

In some embodiments, the method further comprises sequencing the captured nucleic acid. In some embodiments, a sequencing primer anneals to a primer binding site in the adaptor. In some embodiments, the sequencing occurs after amplification. In some embodiments, a sequencing primer anneals to a primer binding site present in the amplification primer. In some embodiments, the captured nucleic acid is 1, 10 or 100 kb long.

In some embodiments, the method does not include intermediate purification steps.

In some embodiments, the invention is a method of sequencing a target nucleic acid in a sample comprising a target nucleic acid and non-target nucleic acids, the method comprising: contacting a double-stranded target nucleic acid having a 3'-end with a catalyst possessing 3'-5'-exonuclease activity thereby generating a first 5'-overhang at the first 5'-end and a first recessed 3'-end in the target nucleic acid; contacting the nucleic acid with an adaptor having a second 5'-overhang at a second 5'-end, the second 5'-overhang capable of hybridizing to the first 5'-overhang thereby forming a hybrid between the first and second 5'-overhangs; linking at least one of the first 3'-end with the second 5'-end thereby forming an adapted nucleic acid; and sequencing the adapted nucleic acid.

In some embodiments, the method further comprises amplifying the captured nucleic acid prior to sequencing. In some embodiments, the sequenced nucleic acid is 1, 10 or 100 kb long.

In some embodiments, the sequencing method includes no intermediate purification steps.

In some embodiments, the invention is a method of enriching nucleic acid from a sample comprising a target nucleic acid and non-target nucleic acids, the method comprising: contacting a double-stranded target nucleic acid having a 3'-end with a catalyst possessing 3'-5'-exonuclease activity thereby generating a first 5'-overhang at the first 5'-end and a first recessed 3'-end in the target nucleic acid; contacting the nucleic acid with an adaptor having a second 5'-overhang at a second 5'-end, the second 5'-overhang capable of hybridizing to the first 5'-overhang thereby forming a hybrid between the first and second 5'-overhangs; wherein the adaptor further comprises a capture moiety; linking at least one of the first 3'-end with the second 5'-end thereby forming an adapted nucleic acid; and capturing the capture moiety on the adaptor thereby enriching the target nucleic acids from the sample.

In some embodiments, the enriched nucleic acid is 1, 10 or 100 kb long.

In some embodiments, the enrichment method includes no intermediate purification steps.

In some embodiments, the invention is a kit for enriching nucleic acid from a sample comprising a target nucleic acid and non-target nucleic acids, the kit comprising: a catalyst possessing 3'-5'-exonuclease activity and capable of generating a 5'-overhang in nucleic acids; an adaptor engineered to have a 5'-overhang at 5'-end, the 5'-overhang capable of hybridizing to a 5'-overhang expected in a target nucleic acid upon treatment with the catalyst; and a DNA ligase.

In some embodiments, the adaptor is double stranded and further comprises a second recessed 3'-end.

In some embodiments, the catalyst possessing a 3'-5' exonuclease activity is a DNA polymerase. In some embodiments, the DNA polymerase possessing a 3'-5' exonuclease activity is a Family A polymerase, a Family B polymerase or a Family C polymerase having the Exo I, Exo II and Exo III domains of the Klenow fragment of the *E. coli* Pol I. In some embodiments, the DNA polymerase has aspartame residues corresponding to the residues D355, D424 and D501 of the Klenow fragment of *E. coli* Pol I. In some embodiments, the DNA polymerase is selected from a group consisting of T4 DNA polymerase, RB69 DNA polymerase, Klenow fragment, T7 DNA polymerase, *E. coli* Pol III delta fragment, eukaryotic pol epsilon, eukaryotic pol delta, and mitochondrial pol gamma.

In some embodiments, the kit further comprises one or more of the dATP, dCTP, dGTP and dTTP.

In some embodiments, the 5'-overhang in the adaptor is 2-15 nucleotides long. In some embodiments, the adaptor comprises at least one of the nucleic acid barcode, a sequencing primer binding site and an amplification primer binding site. In some embodiments, the barcode is selected from a unique molecular ID (UMI) and a sample ID (SID) or both. In some embodiments, the adaptor is formed by annealing of two nucleic acid strands. In some embodiments, the adaptor is formed by exonuclease digestion of the 3'-end to generate the oligonucleotide with the 5'-overhang. In some embodiments, the adaptor comprises a nucleic acid modification increasing the melting temperature of a nucleic acid duplex that includes the modification. In some embodiments, the adaptor comprises a sequence selected from SEQ ID NOs: 7-11. In some embodiments, the adaptor is linked to a capture moiety, i.e., biotin, an antigen capable of binding to a capture antibody, and a capture sequence capable of hybridizing to a capture nucleic acid.

In some embodiments, the kit further comprises a polynucleotide kinase, the reagents for amplification nucleic acids (e.g., an amplification primer capable of annealing to a primer binding site in the adaptor) and reagents for sequencing nucleic acids (e.g., a sequencing primer capable of annealing to a primer binding site in the adaptor. In some embodiments, the amplification primer comprises a sequence selected from SEQ ID NOs: 12-16.

In some embodiments, the invention is a reaction mixture for enriching nucleic acid from a sample comprising a target nucleic acid and non-target nucleic acids, the reaction mixture comprising: a double-stranded target nucleic acid having a 3'-end; a catalyst possessing 3'-5'-exonuclease activity capable of generating a first 5'-overhang at a first 5'-end and a first recessed 3'-end in the target nucleic acid; and an adaptor having a second 5'-overhang at a second 5'-end, the second 5'-overhang capable of hybridizing to the first 5'-overhang, and optionally, a DNA ligase.

DETAILED DESCRIPTION OF THE INVENTION

Definitions

Figure 1:
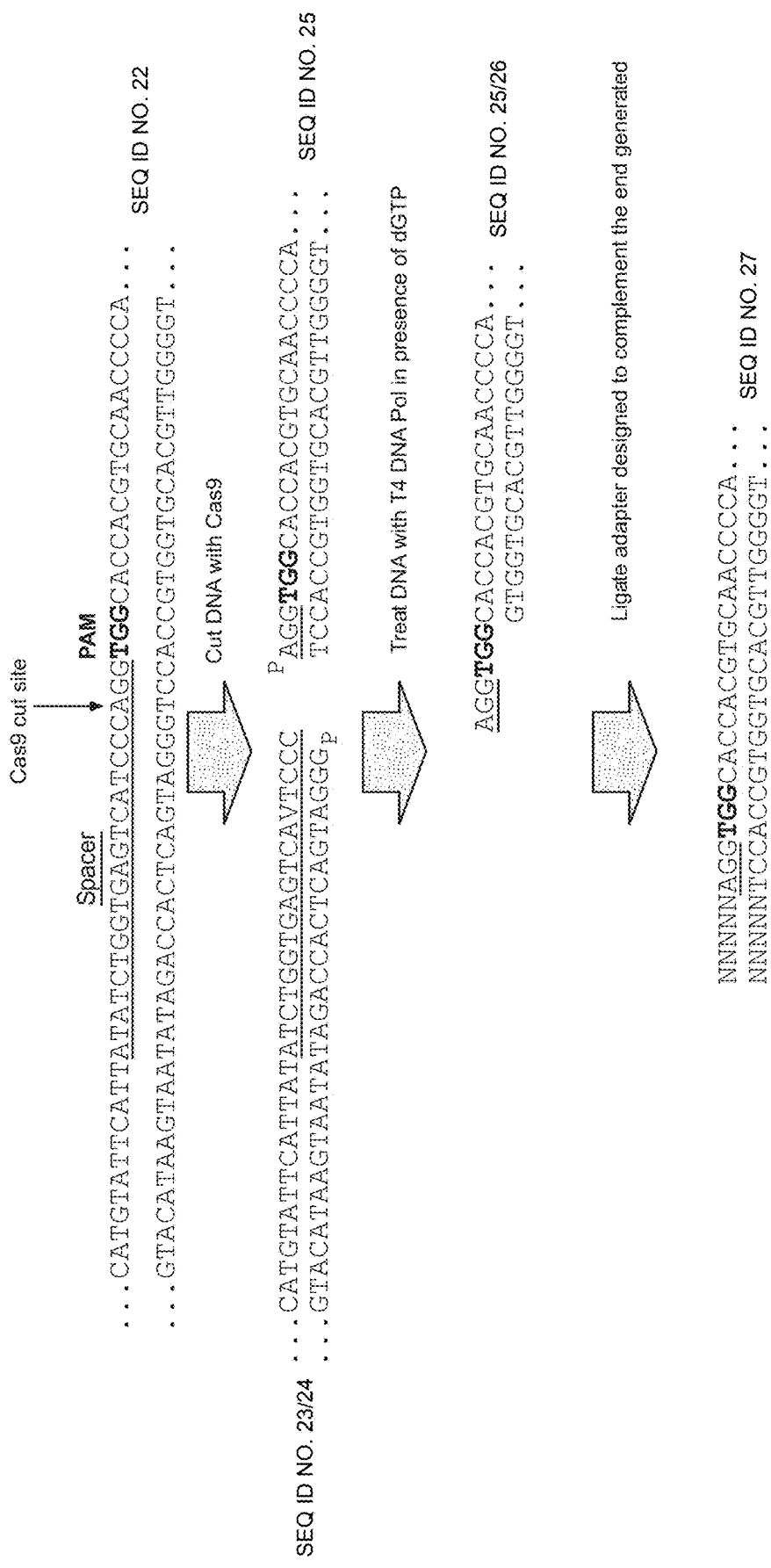
FIG. 1 is a diagram of the method applied to a target sequence cleaved by the CRISPR Cas9 endonuclease. The steps of double-stranded DNA cleavage, exonuclease digestion and adaptor ligation are shown. Figure discloses SEQ ID NOS 22-25 and 25-27, respectively, in order of appearance.

Unless defined otherwise, technical and scientific terms used herein have the same meaning as commonly understood by a person of ordinary skill in the art. See, Sambrook et al., *Molecular Cloning, A Laboratory Manual*, 4$^{th}$ Ed. Cold Spring Harbor Lab Press (2012).

The following definitions are provided to aid in understanding of the disclosure.

The term "endonuclease" refers to an enzyme catalyzing the hydrolysis of a phosphodiester bond between two nucleoside residues within a polynucleotide (DNA or RNA) wherein neither nucleoside residue is a terminal one. An endonuclease can introduce a single-strand break or a double-strand break. A single-strand endonuclease is referred to as "nickase." The double-strand cut may be blunt (blunt ends generated) or staggered (protruding or recessed ends generated).

The term "exonuclease" refers to an enzyme catalyzing the hydrolysis of a phosphodiester bond between a terminal nucleoside residue and a penultimate nucleoside residue within a polynucleotide (DNA or RNA). Exonucleases can be processive or capable of step-wise removal of multiple nucleoside residues from an end of a nucleic acid strand.

The term "CRISPR repeat" or "CRISPR repeat sequence" refers to a minimum CRISPR repeat sequence.

The term "endoribonuclease" to an enzyme that can the hydrolysis of a phosphodiester bond in RNA. In some embodiments, an endoribonuclease can be a site-directed polypeptide. An endoribonuclease may be a member of a CRISPR system (e.g., Type I, Type II, Type III). Endoribonuclease can refer to a Repeat Associated Mysterious Protein (RAMP) superfamily of proteins (e.g., Cas6, Cas6, Cas5 families). Endoribonucleases can also include RNase A, RNase H, RNase I, RNase III family members (e.g., Drosha, Dicer, RNase N), RNase L, RNase P, RNase PhyM, RNase T1, RNase T2, RNase U2, RNase V1, RNase V.

The term "inhibiting" refers to the ability of a chemical structure to partially or completely inhibit a chemical reaction. A skilled artisan would understand that whether the inhibition is partial or complete depends on the sensitivity of detection methods. The term "inhibiting cleavage" with respect to a nuclease refers to the ability to detectably diminish the amount of cleavage product. The term "preventing cleavage" with respect to a nuclease refers to the ability to diminish the amount of cleavage product below the level of detection.

The term "NATNA" refers to a nucleic acid targeting nucleic acid. NATNA may be a part of the programmable endonuclease system, such as a CRISPR system NATNA may be comprised two nucleic acid targeting polynucleotides ("dual guide") including a CRISPR RNA (crRNA) and transactivating CRISPR RNA (tracrRNA). NATNA may be comprised a single nucleic acid targeting polynucleotide ("single guide") comprising crRNA and tracrRNA connected by a fusion region (linker). The crRNA may comprise a targeting region and an activating region. The tracrRNA may comprise a region capable of hybridizing to the activating region of the crRNA. The term "targeting region" refers to a region that is capable of hybridizing to a sequence in a target nucleic acid. The term "activating region" refers to a region that interacts with a polypeptide, e.g., a CRISPR nuclease.

The term "adaptor" refers to a nucleic acid added to nucleic acids in a sample. Typically, the same adaptor is added to a plurality of nucleic acids in a sample. The term "the same adaptor" includes adaptors having the same sequence except for different barcodes (defined below). The term adaptor covers single stranded adaptors, partially single-stranded (interchangeable with partially double-stranded) adaptors and double stranded adaptors. The term "overhang" in relation to a nucleic acid refers to a single-stranded end portion of a partially double stranded nucleic acid. The terms "recessed" and "recessed end" in relation to a nucleic acid refers to an end terminating a double-stranded portion of a partially double stranded nucleic acid. In a partially double stranded nucleic acid, a recessed end of one strand marks the beginning of an overhang on the opposite strand.

The term "barcode" refers to a nucleic acid sequence introduced into another sequence for the purposes of identification. Barcodes can generally be 2 or more and up to about 50 nucleotides long. Barcodes are designed to have at least a minimum number of differences from other barcodes in a sample. Barcodes can be unique to each molecule in a sample or unique to the sample and be shared by multiple molecules in the sample. The term "multiplex identifier," "MID" or "sample identifier," "SID" refer to a barcode that identifies a sample or a source of the sample. As such, all or substantially all, MID barcoded polynucleotides from a single source or sample will share an MID of the same sequence; while all, or substantially all (e.g., at least 90% or 99%), MID barcoded polynucleotides from different sources or samples will have a different MID barcode sequence. Polynucleotides from different sources having different MIDs can be mixed and sequenced in parallel while maintaining the sample information encoded in the MID barcode. The term "unique molecular identifier," "UMI" or "UID," refer to a barcode that identifies a polynucleotide to which it is attached. In some embodiments, all, or substantially all (e.g., at least 90% or 99%), UMI barcodes are unique so that each or substantially each of the UMI-barcoded polynucleotides in a sample has a unique UMI. In other embodiments, the polynucleotides in a sample are tagged non-uniquely so that 1-50% of the polynucleotides in a sample have a UMI that is shared by at least one other polynucleotide as described e.g., in the U.S. Pat. No. 9,902,992.

The term "primer" refers to an oligonucleotide which binds to a specific region of a single-stranded template nucleic acid molecule and initiates nucleic acid synthesis via a polymerase-mediated enzymatic reaction. Typically, a primer comprises fewer than about 100 nucleotides and preferably comprises fewer than about 30 nucleotides. A target-specific primer specifically hybridizes to a target polynucleotide under hybridization conditions. Such hybridization conditions can include, but are not limited to, hybridization in isothermal amplification buffer (20 mM Tris-HCl, 10 mM $(NH_4)_2SO_4$, 50 mM KCl, 2 mM $MgSO_4$, 0.1% TWEEN® 20, pH 8.8 at 25° C.) at a temperature of about 40° C. to about 70° C. In addition to the target-binding region, a primer may have additional regions, typically at the 5'-poriton. The additional region may include universal primer binding site or a barcode.

The term "universal primer" refers to a primer that can hybridize to a universal primer binding site present in a plurality of different nucleic acid in a sample. A universal primer, unlike a target-specific primer is capable of priming amplification of all nucleic acids in the sample without any sequence bias. Universal primer binding sites can be natural or artificial sequences typically added to a target sequence in a non-target-specific manner.

The term "target" or "target nucleic acid" refer to the nucleic acid of interest in the sample. The sample may contain multiple targets as well as multiple copies of each target.

The state-of-the-art methods of capturing and nucleic acids involve dA-tailing and ligation of a dT-tailed adaptor. The dA-tailing and cohesive ligation process involves adding an A nucleotide to the 3'-end of the first nucleic acid (e.g., target or insert) and a T nucleotide to the 3'-end of the second nucleic acid (e.g., adaptor or vector). The dA-tailing method is employed in sequencing and cloning. For example, PCR cloning takes advantage of natural dA-tailing by Taq polymerase and utilizes a dT-tailed vector to enable cohesive end ligation. In making sequencing libraries, the dA-tailing method is applied to randomly fragmented DNA (e.g., sonicated DNA or naturally fragmented cell-free DNA). The dA-tailing method has also been applied to nucleic acids cleaved by endonucleases, including CRISPR endonucleases, see Gilpatrick et al., (2020) *Targeted nanopore sequencing with Cas9-guided adaptor ligation*, Nat. Biotechnol. 38:433. Additionally, SITE-Seq®, a method of genomic sequencing of CRISPR-mediated genome modifications also utilizes the dA-tailing method, see Cameron, P., et al., (2017). *Mapping the genomic landscape of CRISPR-Cas9 cleavage*. Nature methods, 14(6), 600-606.

Alternative methods of generating cohesive ends for ligation involve exonuclease digestion. For example, Gibson assembly involves assembling large stretches of DNA by limited nuclease digestion that creates compatible or semi-compatible DNA ends, see Gibson, D. G., et al., (2009) *Enzymatic assembly of DNA molecules up to several hundred kilobases*, Nat. Methods 6, 343-345, and Gibson, D. G., et al., (2010) *Creation of a Bacterial Cell Controlled by a Chemically Synthesized Genome*, Science 329, 52-56. Earlier, tagged PCR primers and controlled exonuclease digestion were used to generate compatible ends for ligation-independent cloning of PCR products in bacterial cells, see Aslanidis, C. and de Jong, P., (1990) *Ligation-independent cloning of PCR products* (LIC-PCR), Nucleic Acids Res. 18:6069.

The instant invention is an alternative to dA tailing and an improved method of capturing a DNA end generated by a sequence-specific endonuclease (e.g., a restriction endonuclease or a CRISPR endonuclease). The method applies controlled exonuclease activity to the end of a DNA to be captured to excise a defined segment from the 3' end thus creating a 5'-overhang. An adaptor is designed with a 5'-overhang capable of hybridizing to the 5'-overhang in the DNA to be captured. The adaptor (or another nucleic acid partner) forms a specific and stable hybrid with the DNA to be captured. The adaptor may then be covalently attached by a ligase. A direct comparison of the invention to the commonly used 3'-A-overhang adaptor ligation ("dA-tailing method") demonstrates an improvement in ligation specificity and efficiency.

A diagram shown in FIG. 1 illustrates one embodiment of the method. In the example shown in FIG. 1, a double strand break with a blunt end is generated in the target DNA by a CRISPR Cas9 endonuclease. The end is treated with a controlled 3'-5' exonuclease activity. In some embodiments, the controlled exonuclease activity is exhibited by a DNA polymerase in the absence of dNTPs or in the presence of fewer than all 4 dNTPs, e.g., in the presence of only a single dNTP that determines the position at which exonuclease digestion terminates. In the example in FIG. 1, the exonuclease is the T4 DNA polymerase in the presence of only dGTP. In this example, the exonuclease digestion terminates when the T4 DNA polymerase encounters the first G in the strand being digested. In some embodiments, the sequence at the 3'-end to be ligated contains a run of 2-15 nucleotides with only 3 of the 4 bases present. In this way, the dNTP with the $4^{th}$ base can be added to the exonuclease reaction to stop exonuclease activity at the end of the run of 2-15 nucleotides. Adaptors are designed to anneal to the 5' overhang generated by the controlled exonuclease activity. Annealed adaptors are ligated using a ligase.

Figure 2:
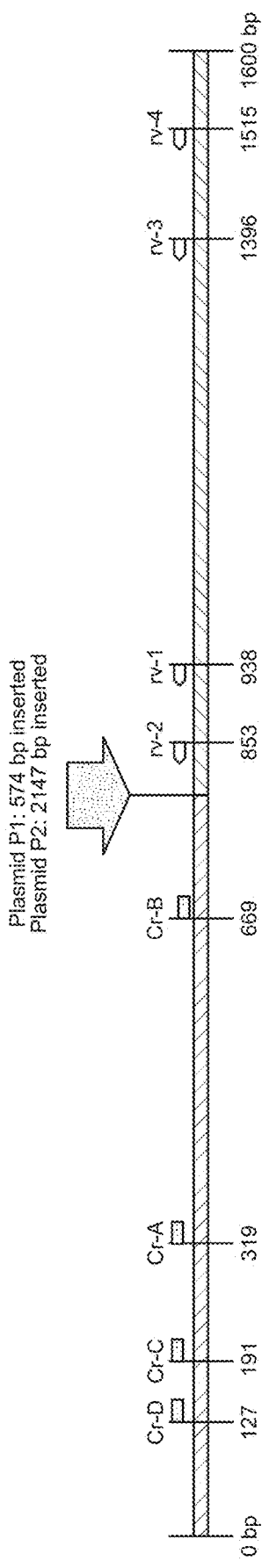
FIG. 2 is a diagram of the target DNA locus showing the location of the endonuclease cleavage site, the CRISPR guide RNA recognition sequences (spacer sequences), and the location of the amplification primer binding sites.

In some embodiments, the method of the invention is compared to the state of the art dA tailing method. In some embodiments, the chosen target is the human T-cell receptor locus (T-cell Receptor Alpha Constant or TRAC locus). In some embodiments, the sequence-specific endonuclease is a CRISPR Cas9 endonuclease and the reaction mixture further comprises a crRNA and a tracrRNA. A crRNAs targeting the TRAC locus is added to guide the sequence-specific Cas9 endonuclease to the TRAC locus. In some embodiments, several crRNAs are designed for the TRAC locus. The map of the locus, the position of crRNAs (Cr-A, B, C, and D) and the cleavage site (arrow) are shown in FIG. 2. In some embodiments, each reaction comprises one of the crRNAs (e.g., Cr-A, B, C, or D, FIG. 2).

Following the exonuclease cleavage, the DNA end downstream of the double-strand cut site is targeted for ligation. For the ligation according to the invention, the reaction mixture is incubated with a DNA polymerase possessing a 3'-5'exonuclease activity (e.g., T4 DNA polymerase) and fewer than 4 dNTPs (e.g., a single dNTP, dGTP for the target sequence shown in FIG. 1).

The dA-tailing and T/A ligation are performed in a parallel reaction according to the state of the art.

Following adapter ligation, optionally, a PCR is performed to amplify the adapted DNA. In some embodiments, the PCR primers comprise a primer that anneals to the adaptor. In some embodiments, the adaptor comprises a universal primer binding site. In some embodiments, the universal primer is paired with a downstream primer capable of hybridizing to the target sequence downstream of the endonuclease cleavage site. In some embodiments, one of the reverse primers shown in FIG. 2 (rv-1, 2, 3, or 4) is used for the TRAC locus.

In some embodiments, the amplified adapted DNA is visualized, e.g., by gel electrophoresis exemplified herein. The results of Examples described herein assessed by gel electrophoresis (FIGS. 3-7) demonstrate that both methods resulted in generation of the expected size PCR products. Notably, in the prior art dA tailing method multiple amplicons are observed (FIG. 3, lanes 3, 4, 7, and 8) indicating that likely multiple adapters ligating to the targeted DNA end. Multimers are not observed in the method of the invention (FIGS. 2, 6 and 7) indicating increased specificity of the method due to longer 5' overhangs of the adapters. Further, comparison of FIG. 5 (genomic DNA, prior art dA-tailing) with the FIGS. 6 and 7 (genomic DNA, instant invention) reveals greater amount of specific product and fewer undesired species indicating greater specificity and efficiency achieved by the invention.

The present invention involves a method of manipulating nucleic acids from a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids that may contain nucleic acids (e.g., urine, sputum, serum, blood or blood fractions, i.e., plasma, lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, or fecal samples). In other embodiments, the sample is a cultured sample, e.g., a tissue culture containing cells and fluids from which nucleic acids may be isolated. In some embodiments, the sample includes formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA). In some embodiments, the nucleic acids of interest in the sample come from infectious agents such as viruses, bacteria, protozoa, or fungi infecting the patient source of the sample. The sample can be collected from a human subject, a non-human subject or from the environment. In some embodiments, the sample is a reaction mixture containing nucleic acids which have undergone one or more in vitro biochemical reactions.

The present invention involves manipulating nucleic acids that were isolated or extracted from a sample. Methods of nucleic acid extraction are well known in the art. See J. Sambrook et al., "Molecular Cloning: A Laboratory Manual," 1989, 2nd Ed., Cold Spring Harbor Laboratory Press: New York, N.Y.). A variety of reagent and kits are commercially available for extracting nucleic acids (DNA or RNA) from biological samples, including products from BD Biosciences (San Jose, Cal.), Clontech (TaKaRa Bio.); Epicentre Technologies (Madison, Wisc.); Gentra Systems, (Minneapolis, Minn.); Qiagen (Valencia, Cal.); Ambion (Austin, Tex.); BioRad Laboratories (Hercules, Cal.); KAPA Biosystems (Roche Sequencing Solutions, Pleasanton, Cal.) and more.

In some embodiments, the invention comprises intermediate purification or separation steps, e.g., to remove unused primers and adaptors, or unligated sample DNA. The purification or separation may be performed by a size selection method selected from gel electrophoresis, affinity chromatography and size exclusion chromatography. In some embodiments, size selection can be performed using Solid Phase Reversible Immobilization (SPRI) technology from Beckman Coulter (Brea, Cal.).

In some embodiments, using compatible buffer systems enables omitting purification or separation steps between the step of forming the recessed 3'-end, the step of ligating the adaptor and the step of further processing the captured nucleic acid e.g., by amplification and/or sequencing.

In some embodiments, the instant invention utilizes a catalyst (enzyme) possessing 3'-5' exonuclease activity. Such activity is present in nucleic acid polymerases and is sometimes referred to as "proof-reading activity," for example in DNA polymerases active in a DNA replication fork. This activity is exhibited in the presence of magnesium ions and in the absence of dNTPs. Compared to exonucleases, such as e.g., Exonuclease III, the speed and extend of the hydrolysis is slow and programmable. If fewer than all four dNTPs are present, the 3'-5' exonuclease activity proceeds until the first nucleotide identical to the dNTP in the reaction is encountered in the strand being cleaved. In the example shown in FIG. 1, it is desired to remove the sequence 3'-TCCACC-5' from the longer sequence 3'-TCCACCGTG . . . -5'. The reaction mixture comprises an enzyme with 3'-5' proofreading exonuclease activity and only dGTP. The exonuclease removes six nucleotides TCCACC until G (corresponding to the dGTP in the reaction mixture) is encountered. The example illustrates that knowing the sequence to be hydrolyzed at the 3'-end, one of skill in the art can engineer a method and a reaction mixture by omitting the correct dNTP or dNTPs so that the 3'-5' exonuclease hydrolysis proceeds up to the desired position and the desired 5'-end protrusion is generated.

The proof-reading 3'-5' exonuclease activity is present in many DNA polymerases of viral, bacterial, and eukaryotic origins. In some embodiments, the catalyst is a DNA polymerase. The DNA polymerases with the 3'-5' proof reading activity comprise the Exo I, Exo II and Exo III domains of the Klenow fragment of the E. coli Pol I. In some embodiments, the DNA polymerase is selected from a Family A polymerase, a Family B polymerase and a Family C polymerase, the polymerase having the Exo I, Exo II and Exo III domains of the Klenow fragment of the E. coli Pol I.

In some embodiments, the DNA polymerase is selected from a Family A polymerase, a Family B polymerase and a Family C polymerase, the polymerase having the DNA polymerase has aspartame residues corresponding to the residues D355, D424 and D501 of the Klenow fragment of E. coli Pol I.

In some embodiments, the DNA polymerase is selected from T4 DNA polymerase, RB69 DNA polymerase, Kienow fragment, T7 DNA polymerase, E. coli Pol III δ (delta) fragment, eukaryotic pol ε (epsilon), eukaryotic pol δ (delta), and mitochondrial pol γ (gamma).

In some embodiments, the DNA polymerase is a wild-type DNA polymerase. In some embodiments, the DNA polymerase is a mutant DNA polymerase having enhanced 3'-5' exonuclease activity. In some embodiments, the mutant DNA polymerase is a T4 DNA polymerase having one or more mutations selected from R335C, L412I, I417V, P424L, Q730S, A737V and A777V.

In some embodiments, the DNA polymerase is a mutant DNA polymerase having reduced 3'-5' exonuclease activity. In some embodiments, the mutant DNA polymerase is a T4 DNA polymerase having one or more mutations selected from D219A, D112A and E114A.

In some embodiments, the end of the double stranded nucleic acid is generated by a sequence-specific endonuclease. In some embodiments, the endonuclease is encoded by the CRISPR locus. The CRISPR (Clustered Regularly Interspaced Short Palindromic Repeats) genomic locus is found many prokaryotic genomes and provides resistance to invasion of foreign nucleic acids. Structure, nomenclature and classification of CRISPR loci are reviewed in Makarova et al., *Evolution and classification of the CRISPR-Cas systems*. Nature Reviews Microbiology. 2011 June; 9(6): 467-477.

Briefly, a typical CRISPR locus includes a number of short repeats regularly interspaced with spacers. The CRISPR locus also includes coding sequences for CRISPR-associated (Cas) genes. A spacer-repeat sequence unit encodes a CRISPR RNA (crRNA). In vivo, a mature crRNAs are processed from a polycistronic transcript referred to as pre-crRNA or pre-crRNA array. The repeats in the pre-crRNA array are recognized by Cas-encoded proteins that bind to and cleave the repeats liberating mature crRNAs. CRISPR systems perform cleavage of a target nucleic acid wherein Cas proteins and crRNA form a CRISPR ribonucleoproteins (crRNP). The crRNA molecule guides the crRNP to the target nucleic acid (e.g., a foreign nucleic acid invading a bacterial cell) and the Cas nuclease proteins cleave the target nucleic acid.

Type I CRISPR systems include means for processing the pre-crRNA array that include a multi-protein complex called Cascade (CRISPR-associated complex for antiviral defense) comprised of subunits CasA, B, C, D and E. The Cascade-crRNA complex recognizes the target nucleic acid through hybridization of the target nucleic acid with crRNA. The bound nucleoprotein complex recruits the Cas3 helicase/nuclease to facilitate cleavage of target nucleic acid.

Type II CRISPR systems include a trans-activating CRISPR RNA (tracrRNA). The tracrRNA hybridizes to a crRNA repeat in the pre-crRNA array and recruits endogenous RNaseIII to cleave the pre-crRNA array. The tracrRNA/crRNA complex can associate with a nuclease, e.g., Cas9. The crRNA-tracrRNA-Cas9 complex recognizes the target nucleic acid through hybridization of the target nucleic acid with crRNA. Hybridization of the crRNA to the target nucleic acid activates the Cas9 nuclease, for target nucleic acid cleavage.

Type III CRISPR systems include the RAMP superfamily of endoribonucleases (e.g., Cas6) that cleave the pre-crRNA array with the help of one or more CRISPR polymerase-like proteins.

Type V CRISPR systems comprise a different set of Cas-like genes, including Csf1, Csf2, Csf3 and Csf4 which are distant homologues of Cas genes in Type I-III CRISPR systems.

CRISPR endonucleases require a nucleic acid targeting nucleic acid (NATNA) also known as guide RNAs. The endonuclease is capable of forming a ribonucleoprotein complex (RNP) with one or more guide RNAs. In some embodiments, the endonuclease is a Type II CRISPR endonuclease and NATNA comprises tracrRNA and crRNA.

In some embodiments, NATNA is selected from the embodiments described in U.S. Pat. No. 9,260,752. Briefly, a NATNA can comprise, in the order of 5' to 3', a spacer extension, a spacer, a minimum CRISPR repeat, a single guide connector, a minimum tracrRNA, a 3' tracrRNA sequence, and a tracrRNA extension. In some instances, a nucleic acid-targeting nucleic acid can comprise, a tracrRNA extension, a 3' tracrRNA sequence, a minimum tracrRNA, a single guide connector, a minimum CRISPR repeat, a spacer, and a spacer extension in any order.

In some embodiments, the guide nucleic acid-targeting nucleic acid can comprise a single guide NATNA. The NATNA comprises a spacer sequence which can be engineered to hybridize to the target nucleic acid sequence. The NATNA further comprises a CRISPR repeat comprising a sequence that can hybridize to a tracrRNA sequence. Optionally, NATNA can have a spacer extension and a tracrRNA extension. These elements can include elements that can contribute to stability of NATNA. The CRISPR repeat and the tracrRNA sequence can interact, to form a base-paired, double-stranded structure. The structure can facilitate binding of the endonuclease to the NATNA.

In some embodiments, the single guide NATNA comprises a spacer sequence located 5' of a first duplex which comprises a region of hybridization between a minimum CRISPR repeat and minimum tracrRNA sequence. The first duplex can be interrupted by a bulge. The bulge facilitates recruitment of the endonuclease to the NATNA. The bulge can be followed by a first stem comprising a linker connecting the minimum CRISPR repeat and the minimum tracrRNA sequence. The last paired nucleotide at the 3' end of the first duplex can be connected to a second linker connecting the first duplex to a mid-tracrRNA. The mid-tracrRNA can comprise one or more additional hairpins.

In some embodiments, the NATNA can comprise a double guide nucleic acid structure. The double guide NATNA comprises a spacer extension, a spacer, a minimum CRISPR repeat, a minimum tracrRNA sequence, a 3' tracrRNA sequence, and a tracrRNA extension. The double guide NATNA does not include the single guide connector. Instead, the minimum CRISPR repeat sequence comprises a 3' CRISPR repeat sequence and the minimum tracrRNA sequence comprises a 5' tracrRNA sequence and the double guide NATNAs can hybridize via the minimum CRISPR repeat and the minimum tracrRNA sequence.

In some embodiments, NATNA is an engineered guide RNA comprising one or more DNA residues (CRISPR hybrid RDNA or chRDNA). In some embodiments, NATNA is selected from the embodiments described in U.S. Pat. No. 9,650,617. Briefly, some chRDNA for use with a Type II CRISPR system may be composed of two strands forming a secondary structure that includes an activating region composed of an upper duplex region, a lower duplex region, a bulge, a targeting region, a nexus, and one or more hairpins. A nucleotide sequence immediately downstream of a targeting region may comprise various proportions of DNA and RNA. Other chRDNA may be a single guide D(R)NA for use with a Type II CRISPR system comprising a targeting region, and an activating region composed of and a lower duplex region, an upper duplex region, a fusion region, a bulge, a nexus, and one or more hairpins. A nucleotide sequence immediately downstream of a targeting region may comprise various proportions of DNA and RNA. For example, the targeting region may comprise DNA or a mixture of DNA and RNA, and an activating region may comprise RNA or a mixture of DNA and RNA.

In some embodiments, the endonuclease generating the 3'-end of a double-stranded target nucleic acid is a restriction endonuclease, e.g., a Type II restriction endonuclease. In some embodiments, the restriction endonuclease generates a blunt end. For each endonuclease, the adaptor of the invention comprises a 5'-overhang capable of hybridizing to the 5'-overhang generated according to the method disclosed herein in excised nucleic acid to be captured.

In embodiments where the endonuclease generating the 3'-end of a double-stranded target nucleic acid is a catalytically inactive CRISPR endonuclease (e.g., catalytically inactive Cas9 or Cas12a) conjugated to the cleavage domain of the restriction endonuclease Fok I. (see e.g., Guilinger, J. P., et al., (2014). *Fusion of catalytically inactive Cas9 to FokI nuclease improves the specificity of genome modification*, Nature biotechnology, 32(6), 577-582.

In embodiments where the endonuclease generating the 3'-end of a double-stranded target nucleic acid is a zinc finger nuclease (ZFN), or a ZFN-Fok I fusion, the target sequence is about 22-52 bases long and comprises a pair of ZFN recognition sequences, each 9-18 nucleotides long, separated by a spacer, which is 4-18 nucleotides long. (see e.g., Kim Y. G., et al., (1996). Hybrid restriction enzymes: zinc finger fusions to Fok I cleavage domain, Proc Natl. Acad. Sci USA. 93(3): 1156-1160.

In embodiments where the endonuclease generating the 3'-end of a double-stranded target nucleic acid is a transcription activator-like effector nuclease (TALEN), or a TALEN-Fok I fusion, the target sequence is about 48-85 nucleotides long and comprises a pair of TALEN recognition sequences, each 18-30 bases long, separated by a spacer, which is 12-25 bases long. (see e.g., Christian M. et al., (2010) Targeting DNA double-strand breaks with TAL effector nucleases, Genetics. 186 (2): 757-61.

As shown in FIG. 1, the methods and compositions disclosed herein utilize the sequence associated with the recognition site and the cleavage site of each endonuclease. In some embodiments, the recognition sequence and the cleavage site are the same. For example, for Type II restriction endonucleases, the recognition site is a palindromic sequence, and the cleavage occurs within the palindromic sequence. In some embodiments, the recognition site is distinct from the cleavage site. In some embodiments, the endonuclease is a CRISPR endonuclease, and the recognition site is a sequence comprising the protospacer adjacent motif (PAM), while the cleavage site is within the region hybridizing to the targeting region of the CRISPR guide RNA (the spacer region). PAM is adjacent to the known stretch of the target sequence.

CRISPR nucleases do not cleave a fixed sequence but instead are guided by a nucleic acid guide as described above. However, the CRISPR nucleases recognize an additional sequence termed protospacer adjacent motif (PAM). The instant invention utilizes the PAM sequence as well as the known sequence of the target nucleic acid to affect the capture of the excised target nucleic acid. As shown in FIG. 1, PAM and the short stretch of the adjacent target sequence are used to design the adaptor oligonucleotide. In some embodiments, the PAM and the short stretch between the PAM and the cleavage site are used to design the 5'-overhang capable of hybridizing the 5'-overhang generated according to the method disclosed herein in excised nucleic acid to be captured.

In some embodiments, the endonuclease generating the 3'-end of a double-stranded target nucleic acid is a CRISPR Class I (CASCADE) endonuclease and the protospacer adjacent motif (PAM) consists of a sequence selected from 5'-AAG-3', 5'-AGG-3', 5'-ATG-3', 5'-GAG-3', 5'-CAG-3', 5'-GTG-3' 5'-TAA-3', 5'-TGG-3, 5'-AAA-3', 5'-AAC-3', 5'-AAT-3'5'-ATA-3', 5'-TAG-3', and 5'-TTG-3'.

In some embodiments, the endonuclease generating the 3'-end of a double-stranded target nucleic acid is a CRISPR Class II endonuclease, and the protospacer adjacent motif (PAM) consists of a sequence selected from 5'-NGG-3', 5'-NGGNG-3', 5'-NNAAAAW-3', 5'-NNNNGATT-3', 5'-GNNNCNNA-3', and 5'-NNNACA-3', 5'-TTN-3', 5'-TTTN-3' and 5'-TTTV-3'.

In some embodiments, the invention utilizes an adaptor added at least one end of a nucleic acid or nucleic acid strand. Adaptor can be single-stranded, double-stranded or partially double-stranded adaptors. The adaptor comprises a double-stranded portion wherein the double-stranded portion is ligated to the double stranded nucleic acid according to the method described herein. Adaptors of various shapes and functions are known in the art, see e.g., U.S. Pat. No. 8,822,150 (Y-shaped adaptor); U.S. Pat. No. 8,455,193 (stem-loop/hairpin adaptor); and U.S. Pat. No. 11,085,084 (various shapes of partially double-stranded adaptors). In some embodiments, the function of an adaptor is to introduce certain useful elements into a nucleic acid. Examples of the adaptor-borne elements include nucleic acid barcodes, amplification primer binding sites, sequencing primer binding sites, enzyme recognition sites, and ligation-enabling sites.

In some embodiments, the adaptor molecules are in vitro synthesized artificial sequences. In other embodiments, the adaptor molecules are in vitro synthesized naturally occurring sequences. In yet other embodiments, the adaptor molecules are isolated naturally occurring molecules or isolated non-naturally occurring molecules.

In some embodiments of the invention, the adaptor is single-stranded, and the 5'-sequence of the adaptor hybridizes to the 5'-overhang of the target nucleic acid, and the 5'-end of the adaptor is ligated to the recessed 3'-end of the target nucleic acid.

In some embodiments of the invention, the adaptor is at least partially double-stranded and comprises a 5'-overhang. The 5'-overhang of the adaptor hybridizes to the 5'-overhang of the target nucleic acid, and the 5'-end of the adaptor is ligated to the recessed 3'-end of the target nucleic acid, while the recessed 3'-end of the adaptor is ligated to the 5'-end of the target nucleic acid.

In the case of a double-stranded adaptor (or an adaptor having a double-stranded portion), the 5'-overhang at the 5'-end of the adaptor is capable or hybridizing to the 5'-overhang of the target nucleic acid and of being ligated to the 3'-end of the target nucleic acid.

In some embodiments, the invention comprises designing an adaptor. The term "designing" refers to the identification of different sequences in the target nucleic acid that can be captured with the adaptor described herein, and further, to designing the 5'-overhang of the adaptor oligonucleotide to enable hybridization to such sequences. As detailed in this disclosure, the method includes generating a 5'-overhang near the cleavage site in the target nucleic acid. The sequence near the cleavage site in the target nucleic acid includes known and unknown sequences. The known sequences include at least a portion of the recognition sequence for the endonuclease near the cleavage site. The known sequence is used to design an exonuclease digestion protocol. The known sequence is further used to design the adaptor oligonucleotide.

For example, FIG. 1 shows a target nucleic acid cleaved by a CRISPR endonuclease where the known sequences adjacent to the end of the nucleic acid include the target sequence, the protospacer adjacent motif (PAM) and a portion of the spacer sequence up to the cleavage site. In this example, the known sequence 5'-AGGTGG(N)$_n$-3' (including the adjacent target sequence) is used to design an exonuclease reaction containing the T4 DNA polymerase and dGTP to generate a 5'-AGGTGG overhang on the target nucleic acid. In this example, the adaptor is designed to have a 5'-overhang containing the sequence 5'-CCACCT-3.'

In the example shown in FIG. 1, cleavage occurs between the $3^{rd}$ and $4^{th}$ nucleotide 5' of the PAM, which is the equivalent of to the position between the $17^{th}$ and $18^{th}$ nucleotides of the spacer. In other embodiments, other CRISPR endonucleases cleave at different positions within the spacer sequence. In some embodiments, the PAM is downstream (3'-side) of the spacer sequence comprising the cleavage site. In some embodiments, the PAM is upstream (5'-side) of the spacer sequence comprising the cleavage site.

Many restriction endonucleases generate cohesive ends that enable easy ligation with a compatible end. However, many restriction endonucleases generate blunt ends, for example Afe I, AluI, BsaAI, BsaBI, BstuI, DpnI, DraI, Eco53kI, EcoRV, FspI, HaeIII, HincII, HpaI, HpyCH4V, Hpy166II, MscI, NaeII, NlaVI, NruI, PmlI, PvuII, RsaI, ScaI, SfoI, SnaBI, SspI, StuI, SwaI and ZraI are some of the blunt cutting enzymes that can be used with the instant method. In the case of a blunt-end cutting restriction endonuclease, the known sequences include the target sequence and the palindromic recognition sequence, which for blunt-end cutters is cleaved via a double-stranded break in the middle of the palindrome. The known sequence is used to design an exonuclease digestion protocol. The known sequence is further used to design the adaptor oligonucleotide. For example, for EcoRV, the recognition sequence is 5'-GATATC-3' which may occur in the target sequence 5'-GATATC-3'. The EcoRV endonuclease cleavage leaves a nucleic acid fragment with 5'-ATC(N)$_n$-3'. The sequence 5'-ATC-3' and any known adjacent sequence is used to design an exonuclease reaction containing the T4 DNA polymerase and the nucleotide adjacent to the C to generate a 5'-ATC overhang on the target nucleic acid. In this example, the adaptor is designed to have a 5'-overhang containing at least the sequence 5'-GAT-3.'

One of skill in the relevant art would recognize that hybridization between nucleic acid strands does not require 100% complementarity or 100% Watson-Crick base-pairing. In some embodiments, a stable hybrid between the 5'-overhang of the adaptor and the 5'-overhang of the target nucleic acid involves canonical (Watson-Crick) base pairs as well as non-canonical base pairs and mismatches. In some embodiments, the adaptor is designed to contain chemically modified nucleic acids, wherein the modification aids in the formation of a stable hybrid. For example, the 5'-overhang of the adaptor may comprise a chemical modification increasing the melting temperature of the double-stranded region. Furthermore, one of skill in the relevant art would recognize that formation of a stable hybrid between nucleic acid strands depends on reaction conditions including ionic strength of the buffer and temperature. Therefore, the adaptor and the reaction conditions are designed and formulated so that the 5'-overhang of the adaptor forms a stable hybrid with the 5'-overhang of the target nucleic acid under the chosen reaction conditions.

Custom synthetic oligonucleotides are readily available from many commercial suppliers utilizing phosphoramidite chemistry including ThermoFisher Scientific, Applied Biosystems (Waltham, Mass.), Biolytic (Newark, Cal.), BioAutomation (Plano, Tex.) and Integrated DNA Technologies (Coralville, Ia.). Other synthesis methods are employed by Twist Bioscience (South San Francisco, Cal.) and Custom Array/GenScript (Redmond, Wash.) Optionally, the custom synthetic oligonucleotides used to form the adaptor described herein may be further purified by any standard methods such as high-performance liquid chromatography (HPLC). Optionally, purification may utilize protective groups such as DMT (dimethoxytrityl). For example, the crude oligonucleotide preparation can be purified by an RP 18 HPLC column (Hypersil, 8×240 mm) using a 0.1 M triethylammonium acetate pH 7.1 acetonitrile gradient. DMT on peak may be collected, desalted via dialysis, evaporated, and dissolved in 10 mM Tris pH 8.0. The OD measured at 260 nm may be determined to assess yield.

The double stranded adaptor oligonucleotide may be prepared by combining the two nucleic acid strands (the strand with an overhang and the strand without the overhang) in a reaction mixture comprising a suitable buffer (e.g., 1×TE or 1.5×TE). To ensure proper annealing without any undesirable secondary structure, the reaction mixture may be heated, e.g., to 90° C. or higher and slowly cooled down. In some embodiments, the partially double-stranded adaptor comprises a single strand assuming a secondary structure, e.g., a dumbbell, stem-loop or a hairpin. Such adaptors may also be formed by subjecting the single strand to heat followed by slowly cooling in the appropriate buffer (e.g., 1×TE or 1.5×TE) to ensure the formation of the desired secondary structure.

In some embodiments, the adaptor includes one or more chemical modifications. In some embodiments, the modification effects increased stability of the double-stranded region of the adaptor. In some embodiments, the modification confers resistance to exonuclease digestion or inhibition of exonucleases.

In some embodiments, the modification is a backbone modification. One type of backbone modification is a modified internucleoside linkage. For example, the modification includes phosphorothioate linkages and heteroatom internucleoside linkages.

Another type of backbone modification is modification of a sugar moiety. In some embodiments, the modification involves incorporation of a 6-membered morpholino ring in place of a ribose or deoxyribose ring. Another backbone modification involves incorporation of a cyclohexenyl ring in place of a ribose or deoxyribose (ceNA). Yet another backbone modification involves incorporation of Locked Nucleic Acids (LNAs) in which the 2'-hydroxyl group is linked to the 4' carbon atom of the ribose thereby forming a bicyclic structure having a 2'-C,4'-C-oxymethylene linkage. LNAs are characterized by duplex stability and resistance to 3'-5' exonuclease digestion.

In some embodiments, the modification is a nitrogenous base modification. For example, the double-stranded nucleic substrate may incorporate one or more 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2

(3H)-one), carbazole cytidine (2H-pyrimido(4,5-b)indol-2-one), pyridoindole cytidine (Hpyrido(3',2':4,5)pyrrolo(2,3-d)pyrimidin-2-one), 7-deaza-adenine, 7-deazaguanosine, 2-aminopyridine and 2-pyridone. Nucleobases can be useful for increasing the binding affinity of a polynucleotide compound. These can include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions can increase nucleic acid duplex stability by 0.6-1.2° C. and can be suitable base substitutions (e.g., when combined with 2'-O-methoxyethyl sugar modifications).

In some embodiments, the double-stranded portion of the adaptor includes a modified nucleotide increasing the melting temperature of the double-stranded portion, e.g., 5-methyl cytosine, 2,6-diaminopurine, 5-hydroxybutynl-2'-deoxyuridine, 8-aza-7-deazaguanosine, a ribonucleotide, a 2'O-methyl ribonucleotide or a locked nucleic acid. In another aspect, the adaptor is modified to inhibit digestion by a nuclease, e.g., by inclusion of a phosphorothioate nucleotide.

In some embodiments, the invention includes the use of a barcode. Analyzing individual nucleic acid molecules by massively parallel sequencing typically requires a separate level of barcoding for sample identification and for error correction. The use of molecular barcodes is described e.g., in U.S. Pat. Nos. 7,393,665, 8,168,385, 8,481,292, 8,685,678, and 8,722,368. A unique molecular identifying barcode (UMI or UID) is added to each molecule to be sequenced to mark the molecule and its progeny (e.g., the original molecule and its amplicons generated by PCR). In some embodiments, a UMI is present in the 5'-portion of an amplification primer. In some embodiments, a UMI is present in an adaptor ligated to the nucleic acid.

The UMI has multiple uses including counting the number of original target molecules in the sample and error correction (Newman, A., et al., (2014) *An ultrasensitive method for quantitating circulating tumor DNA with broad patient coverage*, Nature Medicine doi:10.1038/nm.3519). Briefly, the entire progeny of a single target molecule is marked with the same UMI barcode and forms a barcoded family. A variation in the sequence not shared by all (or the majority) of the members of the barcoded family is discarded as an artefact. UMI barcodes can also be used for positional deduplication and target quantification, as the entire family represents a single molecule in the original sample (Newman, A., et al., (2016) *Integrated digital error suppression for improved detection of circulating tumor DNA*, Nature Biotechnology 34:547). An adaptor comprising a UMI barcode may be conjugated to the nucleic acid to be sequenced.

A sample identifying barcode is used for multiplex sequencing. A multiplex sample ID (MID or SID) barcode used to identify the source of the nucleic acid where two or more samples of nucleic acids are mixed prior to application to a sequencing flowcell.

In some embodiments, the nucleic acid molecule to be sequenced a UMI and an MID. In some embodiments, a single barcode is used as both UMI and MID. In some embodiments, a barcode is composed of several parts. For example, the unique identifying information is comprised of a barcode sequence and a nucleic acid end sequence. In some embodiments, a barcode is comprised of several subcodes as described in the U.S. Patent Application Pub. No. 20200109397 "Modular Nucleic Acid Adaptors."

In some embodiments, each barcode comprises a predefined sequence. In other embodiments, the barcode comprises a random sequence. The barcodes are about 4-20 bases long, so that between 96 and 384 different adaptors, each with a different pair of identical barcodes can be added to a human genomic sample. In some embodiments, the number of UMIs in the reaction can be in excess of the number of molecules to be labelled. A person of ordinary skill would recognize that the number of barcodes depends on the complexity of the sample (i.e., expected number of unique target molecules) and would be able to design and a suitable number of barcodes of suitable lengths for each experiment.

In some embodiments, the invention comprises a ligation step. According to methods widely known in the art (Sambrook et al., *Molecular Cloning, A Laboratory Manual*, 4$^{th}$ Ed. Cold Spring Harbor Lab Press (2012), a ligase enzyme catalyzes joining of a 5'-phosphate moiety (5'-end) with a 3'-hydroxyl moiety (3'-end). The joining forms a covalent bond referred to as a phosphodiester linkage between the end of the nucleic acids. Ligation is catalyzed by a single-strand or a double-strand DNA ligase, e.g., a single-strand DNA ligase such as CircLigase™ ssDNA ligase (Epicentre Biotechnologies, Madison, Wisc., or Lucigen, Middleton, Wisc.), or a double-strand DNA ligase selected from T3 DNA ligase, T4 DNA ligase, T7 DNA ligase, *E. coli* DNA ligase, or any other enzyme capable of efficiently catalyzing the formation of phosphodiester linkages between two nucleic acids.

In some embodiments, the 5'-phosphate moiety is naturally present in the products of endonuclease digestion of the target nucleic acid. In some embodiments, the 5'-phosphate moiety is added to the exonuclease-cleaved target nucleic acid or to the adaptor oligonucleotide. Addition of the 5' phosphate may be accomplished upon the fragment enzymatically, e.g., with a polynucleotide kinase such as T4 polynucleotide kinase.

In some embodiments, the method involves forming a library comprising two or more nucleic acids from a sample. For example, a library may consist of a plurality of different nucleic acids conjugated to adaptors containing the elements needed for library manipulation, including universal amplification primer binding sites, universal sequencing primer binding sites, unique barcodes, or sample-identifying barcodes. The library nucleic acids are ready for sequencing or another type of detection method, e.g., PCR. A library can be stored, and aliquots of the library can be used for multiple rounds of analysis.

In some embodiments, the nucleic acids in the sample comprise all nucleic acids originally found in the sample taken from an organism, a subject (e.g., a patient), or the environment. In some embodiments, the nucleic acids in the sample are enriched. In some embodiments, enrichment is by subtraction, e.g., capture and removal or repetitive sequences or high-abundance sequences or transcripts from an organism's (or subject's) genome (e.g., human Alu sequences, mammalian globin sequences or rRNA sequences present in all cellular organisms). In some embodiments, enrichment is by capture and retention of sequences of interest. In some embodiments, both methods of enrichment are applied, e.g., repetitive or abundant sequences are removed first to facilitate or improve subsequent capture of the sequences of interest from the sample. For enrichment, the capture probes may be free in solution or fixed to solid support.

In some embodiments, enrichment by capture utilizes adaptors ligated to the target nucleic acids as described herein. According to the invention, an adaptor is ligated to the target nucleic acid specifically excised by a sequence-specific nuclease (e.g., a restriction endonuclease or a CRISPR endonuclease). The adaptor serves as a capture probe to capture and separate the target nucleic acids from the sample thereby enriching the target nucleic acid.

In some embodiments, the length of a captured nucleic acid is 1, 10, 50 kb or more.

In some embodiments, the invention is a method of enriching nucleic acid from a sample comprising a target nucleic acid and non-target nucleic acids, the method comprising: contacting a double-stranded target nucleic acid having a 3'-end with a catalyst possessing 3'-5'-exonuclease activity thereby generating a first 5'-overhang at the first 5'-end and a first recessed 3'-end; contacting the nucleic acid with an adaptor having a second 5'-overhang at second the 5'-end, the second 5'-overhang capable of hybridizing to the first 5'-overhang thereby forming a hybrid between the first and second 5'-overhangs; wherein the adaptor further comprises a capture moiety; linking at least one of the first 3'-end with the second 5'-end thereby forming an adapted nucleic acid; and capturing the capture moiety on the adaptor thereby enriching the target nucleic acids from the sample.

For enrichment, a capture probe may comprise a capture moiety. A capture moiety may be any moiety capable of specifically interacting with another capture molecule. Capture moieties—capture molecule pairs include avidin (streptavidin)—biotin, antigen—antibody, magnetic (paramagnetic) particle—magnet, or oligonucleotide—complementary oligonucleotide. The capture molecule can be bound to a solid support so that any nucleic acid on which the capture moiety is present is captured on solid support and separated from the rest of the sample or reaction mixture. In some embodiments, the capture molecule comprises a capture moiety for a secondary capture molecule. For example, a capture moiety may be an oligonucleotide complementary to a capture oligonucleotide (capture molecule). The capture oligonucleotide may be biotinylated and captured on a streptavidin bead. In some embodiments, the adaptor-ligated nucleic acid is enriched via capturing the capture moiety and separating the adaptor-ligated target nucleic acids from unligated nucleic acids in the sample.

In some embodiments, the method includes sequencing the nucleic acid adapted by the methods described herein. Any of a number of sequencing technologies or sequencing assays can be utilized. The term "Next Generation Sequencing (NGS)" as used herein refers to sequencing methods that allow for massively parallel sequencing of single molecules or clonally amplified single molecules.

Non-limiting examples of sequence assays that are suitable for use with the methods disclosed herein include nanopore sequencing (U.S. Pat. Publ. Nos. 2013/0244340, 2013/0264207, 2014/0134616, 2015/0119259 and 2015/0337366), Sanger sequencing, capillary array sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), sequencing by hybridization (Drmanac et al., *Nature Biotech.*, 16:54-58 (1998), and NGS methods, including but not limited to sequencing by synthesis (e.g., HiSeq™, MiSeq™, or Genome Analyzer, each available from Illumina), sequencing by ligation (e.g., SOLiD™, Life Technologies), ion semiconductor sequencing (e.g., Ion Torrent™, Life Technologies), and SMRT® sequencing (e.g., Pacific Biosciences).

Commercially available sequencing technologies include sequencing-by-hybridization platforms from Affymetrix Inc. (Sunnyvale, Calif.), sequencing-by-synthesis platforms from Illumina/Solexa (San Diego, Calif.) and Helicos Biosciences (Cambridge, Mass.), sequencing-by-ligation platform from Applied Biosystems (Foster City, Calif.). Other sequencing technologies include, but are not limited to, the Ion Torrent technology (ThermoFisher Scientific, Waltham, Mass.), Single Molecule Real-Time (SMRT®) sequencing (Pacific Biosciences, Menlo Park, Calif.) and nanopore sequencing (Genia/Stratos Technology from Roche Sequencing Solutions, Santa Clara, Calif.), and Oxford Nanopore Technologies (Oxford, UK).

In some embodiments, the sequencing step involves sequence aligning and determining consensus. In some embodiments, a consensus sequence is determined from a plurality of sequences all having an identical UMI. The sequenced having an identical UMI are presumed to derive from the same original molecule through amplification. In other embodiments, UMI is used to eliminate artifacts, i.e., variations existing in the progeny of a single molecule (characterized by a particular UMI). Such artifacts resulting from PCR errors or sequencing errors can be eliminated using UMIs.

In some embodiments, the number or representation of each sequence in a sample can be quantified by quantifying relative numbers of sequences with each UMI among the population having the same multiplex sample ID (MID). A person skilled in the art will be able to determine the number of sequence reads per UMI ("sequence depth") necessary to determine a consensus sequence. In some embodiments, the desired depth is 5-50 reads per UMI.

The utility of adaptors and amplification primers for introducing additional elements into a library of nucleic acids to be sequenced has been described e.g., in U.S. Pat. Nos. 9,476,095; 9,260,753; 8,822,150; 8,563,478; 7,741,463; 8,182,989; and 8,053,192.

In some embodiments, the invention is a method of sequencing a target nucleic acid in a sample comprising a target nucleic acid and non-target nucleic acids, the method comprising: contacting a double-stranded target nucleic acid having a 3'-end with a catalyst possessing 3'-5'-exonuclease activity thereby generating a first 5'-overhang at the first 5'-end and a first recessed 3'-end; contacting the nucleic acid with an adaptor having a second 5'-overhang at second the 5'-end, the second 5'-overhang capable of hybridizing to the first 5'-overhang thereby forming a hybrid between the first and second 5'-overhangs; linking at least one of the first 3'-end with the second 5'-end thereby forming an adapted nucleic acid; and sequencing the adapted nucleic acid.

In some embodiments, the length of a captured and sequenced nucleic acid is 1, 10, 50 kb or more. Recent advances in nanopore sequencing allow reading 5-20 kb targets when the targets are excised with the CRISPR Cas9 endonuclease and captured by dA tailing and adaptor ligation, see Cas9 Sequencing Kit brochure, cat. SQK-CS9109 from Oxford Nanopore (Oxford, UK). The sequencing technology is capable of reading sequences greater than 50 kb; however, such sequences are not captured with the dA tailing and ligation method, but instead are captured with a transposase-guided insertion of adaptors (tagmentation), see Ultra-Long DNA Sequencing Kit brochure, cat. SQK-ULK0001 from Oxford Nanopore. The instant invention is demonstrated to be more efficient and specific than the dA tailing method and is therefore capable of supplying sequencing short sequencing templates as well as templates longer than 20 kb.

In some embodiments, the invention comprises an amplification step. The adapted nucleic acids formed by the method described herein can be amplified, e.g., prior to sequencing or any other downstream analysis step. The amplification step can involve linear or exponential amplification, e.g., PCR. Amplification may be isothermal or involve thermocycling. In some embodiments, the amplification is exponential and involves PCR or any of its variations including real-time PCR, digital droplet PCR (ddPCR), emulsion PCR and the like.

In some embodiments, a universal primer is used, i.e., a primer that hybridizes to a universal primer binding site present on all nucleic acids in the sample. In some embodiments, a universal primer binding site is present in the adaptor prepared according to the instant invention. In some embodiments, a universal primer binding site is added by extending a primer hybridizing to the adaptor or to the target nucleic acid and comprising the universal primer binding site in the non-hybridizing 5'-region of the primer. All nucleic acids having a universal primer binding site can be amplified with the same universal primer. The number of amplification cycles where universal primers are used can be low, but also can be 10, 20 or as high as 30 or more cycles, depending on the amount of amplification product needed for the subsequent steps. Because amplification with universal primers has reduced sequence bias, the number of amplification cycles need not be limited out of concern for amplification bias.

In some embodiments, a reverse primer is paired with the first universal primer. The reverse primer is designed to hybridize to the target nucleic acid to a strand opposite the strand to which the first universal primer hybridizes. In some embodiments, more than one reverse primer is designed for optimal amplification of the adapted nucleic acid (see FIG. 2 showing an example with four reverse primers rv-1, rv-2, rv-3 and rv-4.). In some embodiments, a reverse primer comprises a binding site for a second universal primer. The second universal primer may be the same or different from the first universal primer. In some embodiments, after a single round or a limited number of rounds of amplification with the reverse primer, only the second universal primer paired with the first universal primer may be used for amplification.

In some embodiments, the invention is a kit for enriching nucleic acid from a sample by the method according to the instant invention. The kit comprises at least a catalyst possessing 3'-5'-exonuclease activity and capable of generating a 5'-overhang in nucleic acids; an adaptor engineered to have a 5'-overhang at 5'-end, the 5'-overhang capable of hybridizing to a 5'-overhang expected in a target nucleic acid upon treatment with the catalyst; and a DNA ligase. The kit may further comprise a polynucleotide kinase.

The adaptor in the kit may be single stranded (i.e., possess a single 5'-end) or double-stranded and have a recessed 3'-end at the terminus with the 5'-overhang.

As described herein, in some embodiments, the catalyst possessing a 3'-5' exonuclease activity is a DNA polymerase such as a Family A polymerase, a Family B polymerase or a Family C polymerase having the Exo I, Exo II and Exo III domains of the Klenow fragment of the *E. coli* Pol I; or a DNA polymerase that has aspartame residues corresponding to the residues D355, D424 and D501 of the Klenow fragment of *E. coli* Pol I, or a DNA polymerase is selected from a group consisting of T4 DNA polymerase, RB69 DNA polymerase, Klenow fragment, T7 DNA polymerase, *E. coli* Pol III delta fragment, eukaryotic pol epsilon, eukaryotic pol delta, and mitochondrial pol gamma.

In some embodiments, the kit further comprising one or more of the dATP, dCTP, dGTP and dTTP.

In some embodiments, the 5'-overhang in the adaptor is 2-15 nucleotides long. In some embodiments, the adaptor comprises at least one of the nucleic acid barcode, a sequencing primer binding site and an amplification primer binding site. The barcode can be a unique molecular ID (UMI) and a sample ID (SID). The adaptor may comprise a nucleic acid modification increasing the melting temperature of a nucleic acid duplex that includes the modification. In some embodiments, adaptor is linked to a capture moiety selected from biotin, an antigen capable of binding to a capture antibody, and a capture sequence capable of hybridizing to a capture nucleic acid.

In some embodiments, the kit includes reagents for amplification nucleic acids, such as a primer capable of annealing to a primer binding site in the adaptor (a universal primer).

In some embodiments, the kit includes reagents for sequencing nucleic acids, such as a sequencing primer capable of annealing to a primer binding site in the adaptor.

In some embodiments, the kit further comprises instructions on performing the method of capturing an excised nucleic acid by a method described herein.

In some embodiments, the invention is a reaction mixture for enriching nucleic acid from a sample. The reaction mixture comprises a double-stranded target nucleic acid having a 3'-end; a catalyst possessing 3'-5'-exonuclease activity capable of generating a first 5'-overhang at a first 5'-end and a first recessed 3'-end in the target nucleic acid; and an adaptor having a second 5'-overhang at a second 5'-end, the second 5'-overhang capable of hybridizing to the first 5'-overhang. The reaction mixture may further comprise a DNA ligase.

In some embodiments, the double-stranded target nucleic acid is 1, 10 or 100 kb long.

The 3'-end of the double-stranded target nucleic acid in the reaction mixture may be a part of a blunt end. The 3'-end of the double-stranded target nucleic acid may be a part of a 3'-overhang. The 3'-end of the double-stranded target nucleic acid may be generated by cleavage of the nucleic acid with a sequence-specific endonuclease, such as a restriction endonuclease, a CRISPR endonuclease, a catalytically inactive CRISPR endonuclease fused to Fok I, a transcription activator-like effector nuclease (TALEN), or a TALEN-Fok I fusion, or a zinc finger nuclease (ZFN), or a ZFN-Fok I fusion.

The catalyst possessing a 3'-5' exonuclease activity in the reaction mixture can be a DNA polymerase. The DNA polymerase may be a Family A polymerase, a Family B polymerase or a Family C polymerase having the Exo I, Exo II and Exo III domains of the Klenow fragment of the *E. coli* Pol I. The DNA polymerase may also be a DNA polymerase with aspartame residues corresponding to the residues D355, D424 and D501 of the Klenow fragment of *E. coli* Pol I. The DNA polymerase may be the T4 DNA polymerase, RB69 DNA polymerase, Klenow fragment, T7 DNA polymerase, *E. coli* Pol III delta fragment, eukaryotic pol epsilon, eukaryotic pol delta, and mitochondrial pol gamma.

In some embodiments, the reaction mixture also includes fewer than four of the dATP, dCTP, dGTP and dTTP, e.g., three, two or only one dNTP.

In some embodiments, the adaptor is double stranded and further comprises a second recessed 3'-end. In some embodiments, the 5'-overhang is 2-15 nucleotides long. The adaptor in the reaction mixture may comprise a nucleic acid barcode (e.g., a unique molecular ID (UMI) or a sample ID (SID)) a sequencing primer binding site and an amplification primer binding site. The adaptor may comprise a nucleic acid modification increasing the melting temperature of a nucleic acid duplex that includes the modification. In some embodiments, the adaptor is linked to a capture moiety selected from biotin, an antigen capable of binding to a capture antibody, and a capture sequence capable of hybridizing to a capture nucleic acid.

EXAMPLES

Example 1. Preparing Reagents

Nucleic Acids: Plasmid and Genomic DNA.

Plasmids 1 and 2 were prepared using the Macherey-Nagel NucleoSpin Plasmid, Mini kit (available from Analytics Shop, Stockbridge, Ga.). Human genomic DNA was prepared using the Gentra Puregene kit (Qiagen, Germantown, Md.) from human peripheral blood mononuclear cells. Genomic DNA was dephosphorylated using New England Biolabs (NEB, Ipswich, Mass.) Quick CIP (catalog #M0525): 5 μg of DNA was incubated with 3 μL of QuickCIP at 37° C. for 10 minutes then 80° C. for 2 minutes in 1× NEB CutSmart® buffer. The map of the DNA target is shown in FIG. 2.

The sequence of Plasmid P1 and P2 differ from the genomic region in that 1) they do not contain the sequences recognized by the Cr-C and Cr-D guides or the rv-3 and rv-4 primer bonding sites; and 2) they contain a 574 or 2147 bp, respectively, insert between the Cr guide sites and the rv primer sites that determine the length of the amplicons generated.

Endonuclease

Preparation of Cas9 Ribonucleoproteins (RNPs). crRNAs and tracrRNA (IDT catalog 1072532) were dissolved in nuclease free water at 100 μM. 1 μL of crRNA (either Cr-A, B, C, or D), 1 μL of tracrRNA, and 8 μL of IDT duplex buffer were combined, then heated to 95° C. for 2 minutes, then allowed to cool to room temperature at 0.1° C. per second resulting in a 10 μM cr:tracr guide stock. A 500 nM Cas9:1000 nM guide RNP stock was made by combining 10 μL of NEB CutSmart® buffer, 79.2 μL of nuclease-free water, 10 μL of 10 μM guide, and 0.8 μL of 10 mg/mL (62 μM) Cas9 protein then incubated at 37° C. for 15 minutes. Aliquots were stored at −80° C.

Adaptors

Adaptor stocks consisted of 5 μM of each oligo in water. 100 μL aliquots were heated to 95° C. for 2 minutes then allowed to cool to room temperature at 0.1° C. per second resulting in a 5 μM adaptor stock. The dA tailing adaptor was made from oligos dA-top and dA-bottom. CRISPR-LE adaptors were made from oligo ABCD-top paired with A-bot, B-bot, C-bot, or D-bot to make specific adaptors for reactions using guides Cr-A, Cr-B, Cr-C, or Cr-D, respectively.

Adaptor and end sequences for each experiment are listed in Table 1 and Table 2. Table 2 further lists the dNTP present in the exonuclease digestion reaction that arrests the progress of exonuclease digestion.

TABLE 1

| | dA Tailing experiment | |
|---|---|---|
| crRNA | Adaptor | SEQ ID NO: |
| Cr-A, B, C or D | $^{5'}$CAGACACTCACACTAATACTCGT$^{3'}$<br>$_{3'}$GTCTGTGAGTGTGATTATGAGCp$_{5'}$ | SEQ ID NO: 5/<br>SEQ ID NO: 6 |
| crRNA | DNA end generated | |
| Cr-A | $^{5'}$pTTGGGGAG...$^{3'}$<br>$_{3'}$AAACCCCTC...$_{5'}$ | |
| Cr-B | $^{5'}$pCACTGGCA...$^{3'}$<br>$_{3'}$AGTGACCGT...$_{5'}$ | |
| Cr-C | $^{5'}$pCGCAGGTG...$^{3'}$<br>$_{3'}$AGCGTCCAC...$_{5'}$ | |
| Cr-D | $^{5'}$pGTAAGGAG...$^{3'}$<br>$_{3'}$ACATTCCTC...$_{5'}$ | |

TABLE 2

| | Nuclease digestion experiment | | |
|---|---|---|---|
| crRNA | Adaptor | Adaptor<br>SEQ ID NO | dNTP in<br>the reaction |
| Cr-A | $^{5'}$CAGACACTCACACTAATACTCG$^{3'}$<br>$_{3'}$GTCTGTGAGTGTGATTATGAGCAACCCCTCTp$_{5'}$ | SEQ ID NO: 7/<br>SEQ ID NO: 8 | dGTP |
| Cr-B | $^{5'}$CAGACACTCACACTAATACTCG$^{3'}$<br>$_{3'}$GTCTGTGAGTGTGATTATGAGCGTGAp$_{5'}$ | SEQ ID NO: 7/<br>SEQ ID NO: 9 | dCTP |
| Cr-C | $^{5'}$CAGACACTCACACTAATACTCG$^{3'}$<br>$_{3'}$GTCTGTGAGTGTGATTATGAGCGCGTCCp$_{5'}$ | SEQ ID NO: 7/<br>SEQ ID NO: 10 | dATP |

TABLE 2-continued

Nuclease digestion experiment

| Cr-D | 5'CAGACACTCACACTAATACTCG3'<br>3'GTCTGTGAGTGTGATTATGAGCCATTCCTCp5' | SEQ ID NO: 7/<br>SEQ ID NO: 11 | dGTP |
|---|---|---|---|

| | DNA end generated | SEQ ID NO | dNTP in the reaction |
|---|---|---|---|
| Cr-A | 5'pTTGGGGAGACCACT...3'<br>3'GGTGA...5' | SEQ ID NO: 17 | dGTP |
| Cr-B | 5'pCACTGGCATCTGG...3'<br>3'CCGTAGACC...5' | SEQ ID NO: 18 | dCTP |
| Cr-C | 5'pCGCAGGTGTT...3'<br>3'ACAA...5' | SEQ ID NO: 19 | dATP |
| Cr-D | 5'pGTAAGGAGCTGCT...3'<br>3'GACGA...5' | SEQ ID NO: 20 | dGTP |

Figure 3:
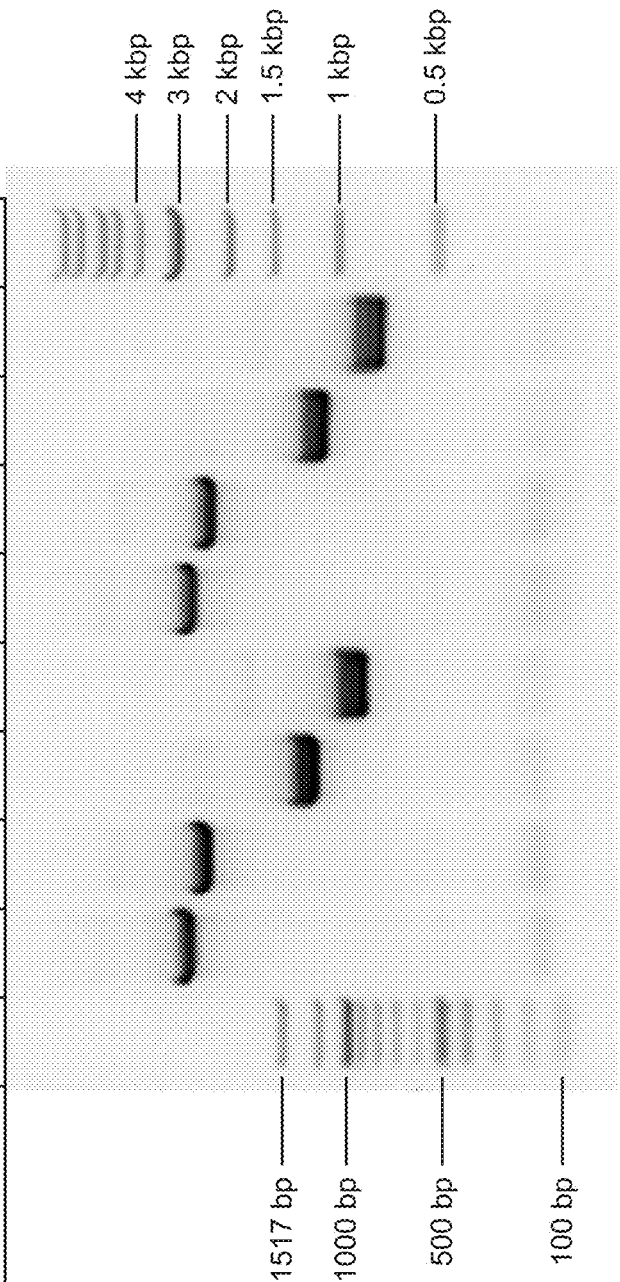
FIG. 3 shows experimental results of the T/A adaptor ligation (prior art) applied to a plasmid DNA target and where the Cas9 ribonucleoprotein (RNP) complex includes guide crRNAs CrA and CrB.
Figure 5:
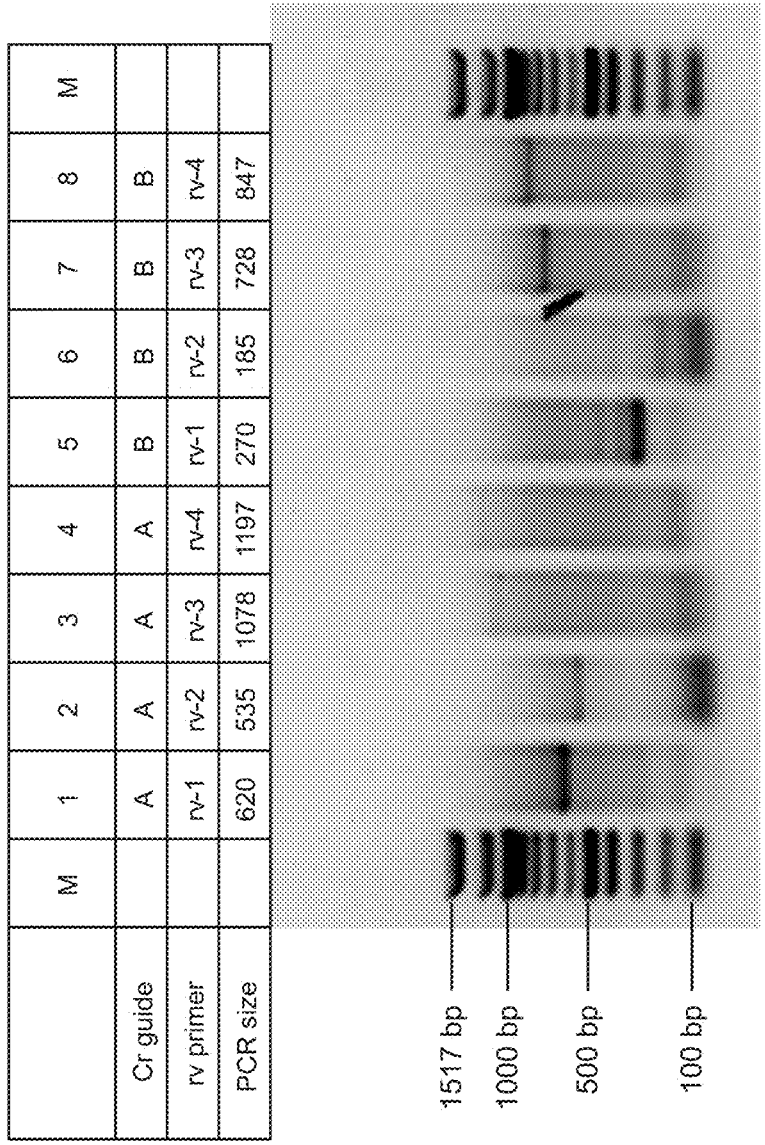
FIG. 5 shows experimental results of the T/A adaptor ligation (prior art) applied to a genomic DNA target and where the Cas9 ribonuclear protein (RNP) complex includes guide crRNAs CrA and CrB.

Example 2. RNP Cleavage and dA-Tailing (Prior Art Method) Applied to Plasmid and Genomic DNA Samples 200 ng of plasmid DNA was combined with 5 μL of RNP (final concentration 100 nM), 1 μL of 10 μM dATP, 1 μL of NEB Taq (catalog #M0273) in 1× CutSmart® buffer in a total of 25 μL. Reactions were incubated at 37° C. for 15 minutes then 72° C. for 5 minutes (in order to remove Cas9 from the target DNA and allow Taq addition of dA tail). Samples were SPRI cleaned before proceeding to the ligation step. The procedure was identical for genomic DNA samples, except that 1 μg of dephosphorylated genomic DNA was substituted for 200 ng of plasmid DNA. The results for plasmid DNA are shown in FIG. 3, and the results for genomic DNA are shown in FIG. 5.

Example 3. RNP Cleavage and CRISPR-LE Method (Invention) Applied to Plasmid and Genomic DNA Samples 200 ng of plasmid DNA was combined with 5 μL of RNP (final concentration 100 nM) in 1× CutSmart® buffer in a total of 25 μL. Reactions were incubated at 37° C. for 15 minutes then 72° C. for 5 minutes (in order to remove Cas9 from the target DNA). DNA was purified with 0.8× SPRI and eluted with 15 μL of water. All 15 μL of DNA was then treated 1 μL of 0.067 mg/mL T4 DNA polymerase, 2.5 mM of the appropriate dNTP, 10 mM Tris-HCl pH 8.0, 50 mM NaCl, 10 mM MgCl₂, 1 mM DTT in a 20 μL volume and incubated at 22° C. for 30 minutes then 75° C. for 20 minutes. DNA was purified with 0.8× SPRI and eluted with 15 μL of water before proceeding to the ligation step. The procedure was identical for genomic DNA samples except that 1 μg of dephosphorylated genomic DNA was substituted for 200 ng of plasmid DNA.

Figure 4:
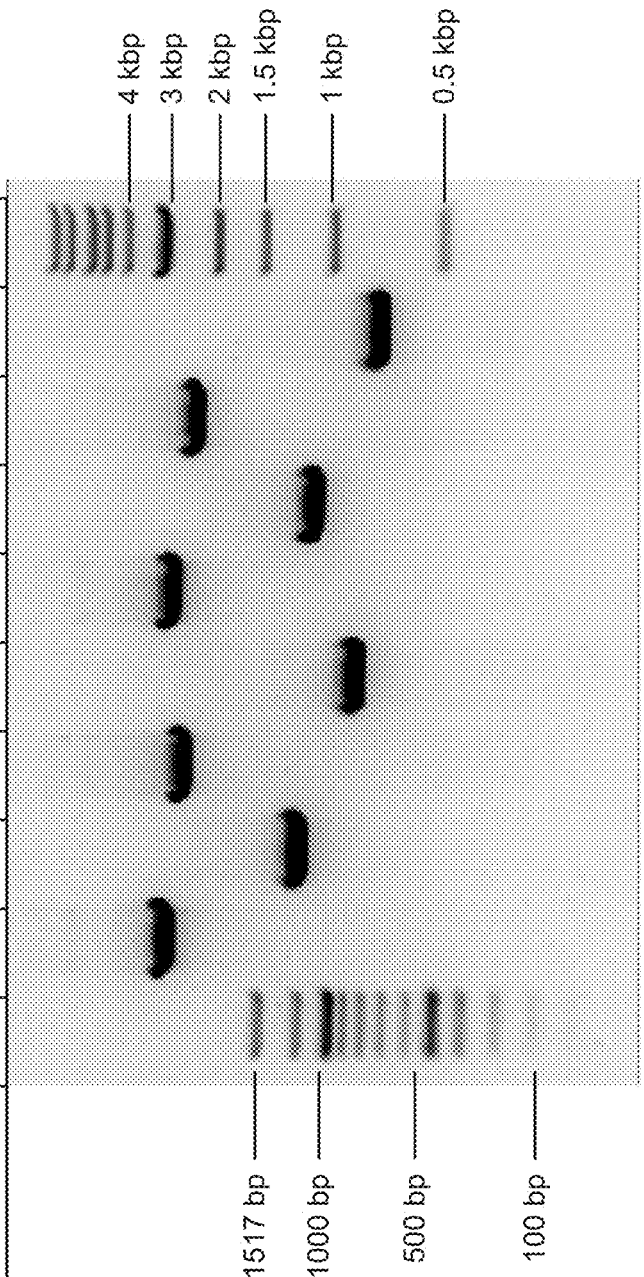
FIG. 4 shows experimental results of the method of the invention applied to a plasmid DNA target and where the Cas9 ribonuclear protein (RNP) complex includes guide crRNAs CrA and CrB.
Figure 6:
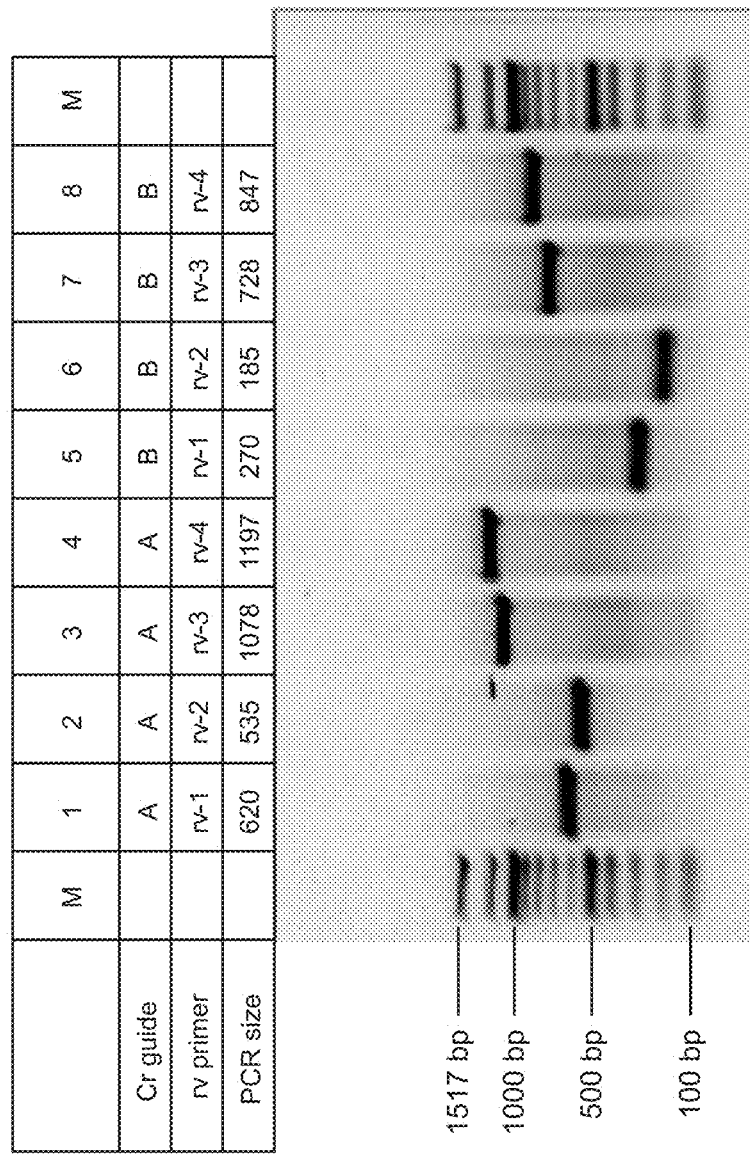
FIG. 6 shows experimental results of the method of the invention applied to a genomic DNA target and where the Cas9 ribonuclear protein (RNP) complex includes guide crRNAs CrA and CrB.
Figure 7:
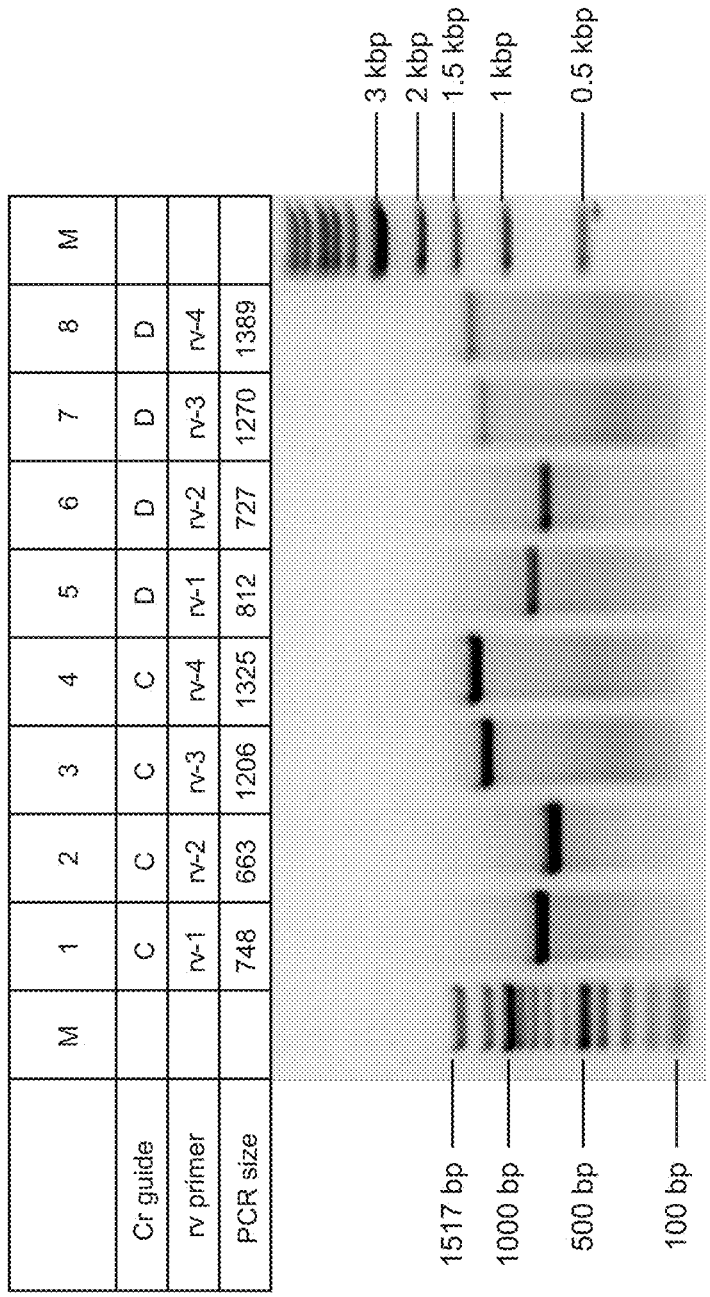
FIG. 7 shows experimental results of the method of the invention applied to a genomic DNA target, where the Cas9 ribonuclear protein (RNP) complex includes guide crRNAs CrC and CrD.

The results for plasmid DNA are shown in FIG. 4, and the results for genomic DNA are shown in FIG. 6 (crRNAs CrA and CrB) and in FIG. 7 (crRNAs CrC and CrD).

Example 4. Intermediate Purification Steps

SPRI cleanups. SPRI cleanups were performed using Beckman Coulter SPRIselect reagent kit (catalog #B23317). Reaction volumes were first adjusted to 100 μL with water then 0.8× SPRI beads added. DNA-SPRI mixtures were incubated on a magnetic stand for 4 minutes, then the supernatant was removed. Beads were washed 2 times by the addition of 85% ethanol then eluted in 15 μL of water.

Example 5. Ligation of Adaptors

SPRI cleaned DNA (15 μL) samples were combined with 1 μL of NEB Quick Ligase (catalog #M2200) and 250 nM adaptor in 1× NEB Quick Ligase Buffer (catalog #B6058S) in a 20 μL reaction volume and incubated for 20 minutes at room temperature. Ligations were cleaned using 0.8× SPRI and eluted with 20 μL of water before proceeding to the PCR step.

Example 6. Amplification

20 μL PCRs consisted of 0.2 μL NEB Q5 Hot Start High Fidelity DNA Polymerase (catalog #M0493), 2 μL of adaptor-ligated DNA, 500 nM forward primer (F), 500 nM the appropriate reverse primer (rv-1, 2, 3, or 4), 200 nM each NTP, in 1× Q5 Reaction Buffer. Thermocycling conditions were as follows: 98° C. for 30 seconds, (98° C. 10 seconds, 58° C. 30 seconds, 72° C. 45 seconds) 32 times, 72° C. 2 minutes.

Example 7. Gel Electrophoresis

10 μL of each PCR was run on a 1% agarose-TAE gels at 90 volts for 60 minutes and imaged on a Bio-Rad Gel Doc EZ Imaging System. Expected amplicon sizes (in bp) for each configuration are listed in Table 3.

TABLE 3

| Expected amplicon sizes | | | |
|---|---|---|---|
| | Rev. | Expected amplicon size, bp | | |
| crRNA | primer | Genomic DNA | Plasmid P1 | Plasmid P2 |
| Cr-A | rv-1 | 620 | 1194 | 2767 |
| Cr-A | rv-2 | 535 | 1109 | 2682 |
| Cr-A | rv-3 | 1078 | 1652 | 3225 |
| Cr-A | rv-4 | 1197 | 1771 | 3344 |
| Cr-B | rv-1 | 270 | 844 | 2417 |

TABLE 3-continued

Expected amplicon sizes

| crRNA | Rev. primer | Expected amplicon size, bp | | |
|---|---|---|---|---|
| | | Genomic DNA | Plasmid P1 | Plasmid P2 |
| Cr-B | rv-2 | 185 | 759 | 2332 |
| Cr-B | rv-3 | 728 | 1302 | 2875 |
| Cr-B | rv-4 | 847 | 1421 | 2994 |
| Cr-C | rv-1 | 748 | 1322 | 2895 |
| Cr-C | rv-2 | 663 | 1237 | 2810 |
| Cr-C | rv-3 | 1206 | 1780 | 3353 |
| Cr-C | rv-4 | 1325 | 1899 | 3472 |
| Cr-D | rv-1 | 812 | 1386 | 2959 |
| Cr-D | rv-2 | 727 | 1301 | 2874 |
| Cr-D | rv-3 | 1270 | 1844 | 3417 |
| Cr-D | rv-4 | 1389 | 1963 | 3536 |

While the invention has been described in detail with reference to specific examples, it will be apparent to one skilled in the art that various modifications can be made within the scope of this invention. Thus, the scope of the invention should not be limited by the examples described herein, but by the claims presented below.

INFORMAL SEQUENCE LISTING

| Oligo name | SEQ ID NO | Sequence in the 5'-3' direction |
|---|---|---|
| Cr-A | SEQ ID NO: 1 | CTAATGCCCAGCCTAAGTTG |
| Cr-B | SEQ ID NO: 2 | GCCCCGCCCTTGTCCATCAC |
| Cr-C | SEQ ID NO: 3 | TAGTGCTGGGGCTTAGACGC |
| Cr-D | SEQ ID NO: 4 | GGTGAAATTCCTGAGATGTA |
| dA-top | SEQ ID NO: 5 | CAGACACTCACACTAATACTCGT |
| dA-bottom | SEQ ID NO: 6 | pCGAGTATTAGTGTGAGTGTCTG |
| ABCD-top | SEQ ID NO: 7 | CAGACACTCACACTAATACTCG |
| A-bottom | SEQ ID NO: 8 | pTCTCCCCAACGAGTATTAGTGTGAGTGTCTG |
| B-bottom | SEQ ID NO: 9 | pAGTGCGAGTATTAGTGTGAGTGTCTG |
| C-bottom | SEQ ID NO: 10 | pCCTGCGCGAGTATTAGTGTGAGTGTCTG |
| D-bottom | SEQ ID NO: 11 | pCTCCTTACCGAGTATTAGTGTGAGTGTCTG |
| rv-1 | SEQ ID NO: 12 | TGAAGTCCATAGACCTCATGTC |
| rv-2 | SEQ ID NO: 13 | ATCAAAATCGGTGAATAGGCAG |
| rv-3 | SEQ ID NO: 14 | GGAGAAATAAGGAGAGGCAAC |
| rv-4 | SEQ ID NO: 15 | TAATTCCTCCACTTCAACACC |
| F | SEQ ID NO: 16 | CAGACACTCACACTAATACTCG |

Key:

| Oligo name | Description |
|---|---|
| Cr-A | Targeting region of crRNA A |
| Cr-B | Targeting region of crRNA B |
| Cr-C | Targeting region of crRNA C |
| Cr-D | Targeting region of crRNA D |
| dA-top | Top strand, adaptor used in the dA tailing experiment |
| dA-bottom | Bottom strand, adaptor used in the dA tailing experiment |
| ABCD-top | Top strand shared among adaptors A-D (endonuclease experiment) |
| A-bot | Bottom strand, adaptor A (endonuclease experiment) |
| B-bot | Bottom strand, adaptor B (endonuclease experiment) |
| C-bot | Bottom strand, adaptor C (endonuclease experiment) |

-continued

| INFORMAL SEQUENCE LISTING |
| --- |
| D-bot         Bottom strand, adaptor D (endonuclease experiment) |
| rv-1          Reverse PCR primer 1 |
| rv-2          Reverse PCR primer 2 |
| rv-3          Reverse PCR primer 3 |
| rv-4          Reverse PCR primer 4 |
| F             Forward PCR primer |

SEQ ID NO: 21 TRAC genomic sequence (1600 bp) shown in FIG. 2:
GGCTCCAACTAACATTTGTTTGGTACTTTACAGTTTATTAAATAGATGTTTATATG

GAGAAGCTCTCATTTCTTTCTCAGAAGAGCCTGGCTAGGAAGGTGGATGAGGCA

CCATATTCATTTTGCAGGTGAAATTCCTGAGATGTAAGGAGCTGCTGTGACTTGC

TCAAGGCCTTATATCGAGTAAACGGTAGTGCTGGGGCTTAGACGCAGGTGTTCTG

ATTTATAGTTCAAAACCTCTATCAATGAGAGAGCAATCTCCTGGTAATGTGATAG

ATTTCCCAACTTAATGCCAACATACCATAAACCTCCCATTCTGCTAATGCCCAGC

CTAAGTTGGGGAGACCACTCCAGATTCCAAGATGTACAGTTTGCTTTGCTGGGCC

TTTTTCCCATGCCTGCCTTTACTCTGCCAGAGTTATATTGCTGGGGTTTTGAAGAA

GATCCTATTAAATAAAAGAATAAGCAGTATTATTAAGTAGCCCTGCATTTCAGGT

TTCCTTGAGTGGCAGGCCAGGCCTGGCCGTGAACGTTCACTGAAATCATGGCCTC

TTGGCCAAGATTGATAGCTTGTGCCTGTCCCTGAGTCCCAGTCCATCACGAGCAG

CTGGTTTCTAAGATGCTATTTCCCGTATAAAGCATGAGACCGTGACTTGCCAGCC

CCACAGAGCCCCGCCCTTGTCCATCACTGGCATCTGGACTCCAGCCTGGGTTGGG

GCAAAGAGGGAAATGAGATCATGTCCTAACCCTGATCCTCTTGTCCCACAGATAT

CCAGAACCCTGACCCTGCCGTGTACCAGCTGAGAGACTCTAAATCCAGTGACAA

GTCTGTCTGCCTATTCACCGATTTTGATTCTCAAACAAATGTGTCACAAAGTAAG

GATTCTGATGTGTATATCACAGACAAAACTGTGCTAGACATGAGGTCTATGGACT

TCAAGAGCAACAGTGCTGTGGCCTGGAGCAACAAATCTGACTTTGCATGTGCAA

ACGCCTTCAACAACAGCATTATTCCAGAAGACACCTTCTTCCCCAGCCCAGGTAA

GGGCAGCTTTGGTGCCTTCGCAGGCTGTTTCCTTGCTTCAGGAATGGCCAGGTTC

TGCCCAGAGCTCTGGTCAATGATGTCTAAAACTCCTCTGATTGGTGGTCTCGGCC

TTATCCATTGCCACCAAAACCCTCTTTTTACTAAGAAACAGTGAGCCTTGTTCTG

GCAGTCCAGAGAATGACACGGGAAAAAAGCAGATGAAGAGAAGGTGGCAGGAG

AGGGCACGTGGCCCAGCCTCAGTCTCTCCAACTGAGTTCCTGCCTGCCTGCCTTT

GCTCAGACTGTTTGCCCCTTACTGCTCTTCTAGGCCTCATTCTAAGCCCCTTCTCC

AAGTTGCCTCTCCTTATTTCTCCCTGTCTGCCAAAAAATCTTTCCCAGCTCACTAA

GTCAGTCTCACGCAGTCACTCATTAACCCACCAATCACTGATTGTGCCGGCACAT

GAATGCACCAGGTGTTGAAGTGGAGGAATTAAAAAGTCAGATGAGGGGTGTGCC

CAGAGGAAGCACCATTCTAGTTGGGGGAGCCCATCTGTCAGCTGGGAAAAGTCC

AAATAACT

What is claimed is:

1. A method of capturing a nucleic acid from a sample comprising a target nucleic acid and non-target nucleic acids, the method comprising:
   a) contacting a double-stranded target nucleic acid having a 3'-end generated by cleavage of the nucleic acid with a CRISPR Cas9 endonuclease in complex with a guide RNA or chRDNA wherein the endonuclease cleaves the target nucleic acid adjacent to a protospacer adjacent motif (PAM), with fewer than four of dATP, dCTP, dGTP and dTTP and with a DNA polymerase possessing 3'-5' exonuclease activity, wherein the 3'-5' exonuclease activity is exhibited in the presence of fewer than four of dATP, dCTP, dGTP and dTTP, and the 3'-5' exonuclease activity stops at the nucleotide identical to one or more of the dATP, dCTP, dGTP and dTTP present, thereby generating a first 5'-overhang and a first recessed 3'-end in the target nucleic acid;
   b) contacting the nucleic acid with an adaptor having a second 5'-overhang capable of hybridizing to the first 5'-overhang thereby forming a hybrid between the first and second 5'-overhangs, wherein the second 5'overhang comprises a sequence adjacent to the PAM and the PAM, and
   c) linking the 5'-end of the overhang in the target nucleic acid with the recessed 3'-end of the adaptor, and linking the 5'-end of the overhang in the adaptor with the recessed 3'-end of the target nucleic acid, thereby capturing the target nucleic acid by forming an adapted nucleic acid.

2. The method of claim 1, wherein the DNA polymerase is selected from the group consisting of: T4 DNA polymerase, RB69 DNA polymerase, Klenow fragment of the *E. coli* Pol I, T7 DNA polymerase, *E. coli* Pol III delta fragment, eukaryotic pol epsilon, eukaryotic pol delta, and mitochondrial pol gamma.

3. The method of claim 1, wherein the 5'-overhang generated by the DNA polymerase possessing the 3'-5' exonuclease activity is 2-15 nucleotides long.

4. The method of claim 1, wherein the adaptor comprises at least one of a nucleic acid barcode selected from a unique molecular ID (UMI) and a sample ID (SID), a sequencing primer binding site and an amplification primer binding site.

5. The method of claim 1, wherein the adaptor comprises a sequence selected from SEQ ID NOs: 7-11.

6. The method of claim 1, further comprising amplifying the captured nucleic acid.

7. The method of claim 6, wherein an amplification primer anneals to a primer binding site in the adaptor and the amplification primer comprises a sequence selected from SEQ ID NOs: 12-16.

8. The method of claim 1, wherein the adaptor is linked to a capture moiety, and the method further comprises capturing the capture moiety in the adapted nucleic acid thereby capturing the nucleic acid.

9. The method of claim 8, wherein the capture moiety is selected from biotin, an antigen capable of binding to a capture antibody, and a capture sequence capable of hybridizing to a capture nucleic acid.

10. The method of claim 1, further comprising sequencing the captured nucleic acid.

11. The method of claim 10, wherein the captured nucleic acid is amplified prior to the sequencing and the amplification uses an amplification primer that anneals to a binding site in the adaptor, and wherein a sequencing primer anneals to a primer binding site present in the amplification primer.

12. The method of claim 1, wherein the captured nucleic acid is 1, 10 or 100 kb long.

13. The method of claim 1, wherein no purification steps are performed between steps a) and b) or a) and c).

\* \* \* \* \*

UNITED STATES PATENT AND TRADEMARK OFFICE
CERTIFICATE OF CORRECTION

| | |
|---|---|
| PATENT NO. | : 12,416,045 B2 |
| APPLICATION NO. | : 18/715913 |
| DATED | : September 16, 2025 |
| INVENTOR(S) | : Scott David Gradia |

It is certified that error appears in the above-identified patent and that said Letters Patent is hereby corrected as shown below:

In the Specification

Column 1, Line 10, insert the following:
--CROSS-REFERENCE TO RELATED APPLICATIONS
This application is a U.S. national stage of the International Application Ser. No. PCT/US2022/080938 filed on December 5, 2022, which claims priority to the U.S. Provisional Application Ser. No. 63/286,922 filed on December 7, 2021, all incorporated herein by reference.--

Signed and Sealed this
Twenty-first Day of October, 2025

John A. Squires
*Director of the United States Patent and Trademark Office*

SEQUENCE LISTING

```
Sequence total quantity: 27
SEQ ID NO: 1              moltype = DNA   length = 20
FEATURE                   Location/Qualifiers
misc_feature              1..20
                          note = Synthetic: Cr-A
source                    1..20
                          mol_type = other DNA
                          organism = synthetic construct
SEQUENCE: 1
ctaatgccca gcctaagttg                                                20

SEQ ID NO: 2              moltype = DNA   length = 20
FEATURE                   Location/Qualifiers
misc_feature              1..20
                          note = Synthetic: Cr-B
source                    1..20
                          mol_type = other DNA
                          organism = synthetic construct
SEQUENCE: 2
gccccgccct tgtccatcac                                                20

SEQ ID NO: 3              moltype = DNA   length = 20
FEATURE                   Location/Qualifiers
misc_feature              1..20
                          note = Synthetic: Cr-C
source                    1..20
                          mol_type = other DNA
                          organism = synthetic construct
SEQUENCE: 3
tagtgctggg gcttagacgc                                                20

SEQ ID NO: 4              moltype = DNA   length = 20
FEATURE                   Location/Qualifiers
misc_feature              1..20
                          note = Synthetic: Cr-D
source                    1..20
                          mol_type = other DNA
                          organism = synthetic construct
SEQUENCE: 4
ggtgaaattc ctgagatgta                                                20

SEQ ID NO: 5              moltype = DNA   length = 23
FEATURE                   Location/Qualifiers
misc_feature              1..23
                          note = Synthetic: dA-top
source                    1..23
                          mol_type = other DNA
                          organism = synthetic construct
SEQUENCE: 5
cagacactca cactaatact cgt                                            23

SEQ ID NO: 6              moltype = DNA   length = 22
FEATURE                   Location/Qualifiers
misc_feature              1..22
                          note = Synthetic: dA-bottom
modified_base             1
                          mod_base = OTHER
                          note = 5'-phosphate
source                    1..22
                          mol_type = other DNA
                          organism = synthetic construct
SEQUENCE: 6
cgagtattag tgtgagtgtc tg                                             22

SEQ ID NO: 7              moltype = DNA   length = 22
FEATURE                   Location/Qualifiers
misc_feature              1..22
                          note = Synthetic: ABCD-top
source                    1..22
                          mol_type = other DNA
                          organism = synthetic construct
SEQUENCE: 7
cagacactca cactaatact cg                                             22

SEQ ID NO: 8              moltype = DNA   length = 31
FEATURE                   Location/Qualifiers
misc_feature              1..31
                          note = Synthetic: A-bottom
```

```
modified_base           1
                        mod_base = OTHER
                        note = 5'-phosphate
source                  1..31
                        mol_type = other DNA
                        organism = synthetic construct
SEQUENCE: 8
tctccccaac gagtattagt gtgagtgtct g                              31

SEQ ID NO: 9            moltype = DNA  length = 26
FEATURE                 Location/Qualifiers
misc_feature            1..26
                        note = Synthetic: B-bottom
modified_base           1
                        mod_base = OTHER
                        note = 5'-phosphate
source                  1..26
                        mol_type = other DNA
                        organism = synthetic construct
SEQUENCE: 9
agtgcgagta ttagtgtgag tgtctg                                    26

SEQ ID NO: 10           moltype = DNA  length = 28
FEATURE                 Location/Qualifiers
misc_feature            1..28
                        note = Synthetic: C-bottom
modified_base           1
                        mod_base = OTHER
                        note = 5'-phosphate
source                  1..28
                        mol_type = other DNA
                        organism = synthetic construct
SEQUENCE: 10
cctgcgcgag tattagtgtg agtgtctg                                  28

SEQ ID NO: 11           moltype = DNA  length = 30
FEATURE                 Location/Qualifiers
misc_feature            1..30
                        note = Synthetic: D-bottom
modified_base           1
                        mod_base = OTHER
                        note = 5'-phosphate
source                  1..30
                        mol_type = other DNA
                        organism = synthetic construct
SEQUENCE: 11
ctccttaccg agtattagtg tgagtgtctg                                30

SEQ ID NO: 12           moltype = DNA  length = 22
FEATURE                 Location/Qualifiers
misc_feature            1..22
                        note = Synthetic: rv-1
source                  1..22
                        mol_type = other DNA
                        organism = synthetic construct
SEQUENCE: 12
tgaagtccat agacctcatg tc                                        22

SEQ ID NO: 13           moltype = DNA  length = 22
FEATURE                 Location/Qualifiers
misc_feature            1..22
                        note = Synthetic: rv-2
source                  1..22
                        mol_type = other DNA
                        organism = synthetic construct
SEQUENCE: 13
atcaaaatcg gtgaataggc ag                                        22

SEQ ID NO: 14           moltype = DNA  length = 21
FEATURE                 Location/Qualifiers
misc_feature            1..21
                        note = Synthetic: rv-3
source                  1..21
                        mol_type = other DNA
                        organism = synthetic construct
SEQUENCE: 14
ggagaaataa ggagaggcaa c                                         21

SEQ ID NO: 15           moltype = DNA  length = 21
```

```
FEATURE                 Location/Qualifiers
misc_feature            1..21
                        note = Synthetic: rv-4
source                  1..21
                        mol_type = other DNA
                        organism = synthetic construct
SEQUENCE: 15
taattcctcc acttcaacac c                                              21

SEQ ID NO: 16           moltype = DNA  length = 22
FEATURE                 Location/Qualifiers
misc_feature            1..22
                        note = Synthetic: F
source                  1..22
                        mol_type = other DNA
                        organism = synthetic construct
SEQUENCE: 16
cagacactca cactaatact cg                                             22

SEQ ID NO: 17           moltype = DNA  length = 14
FEATURE                 Location/Qualifiers
misc_feature            1..14
                        note = Synthetic: Cr-A
modified_base           1
                        mod_base = OTHER
                        note = 5'-phosphate
source                  1..14
                        mol_type = other DNA
                        organism = synthetic construct
SEQUENCE: 17
ttggggagac cact                                                      14

SEQ ID NO: 18           moltype = DNA  length = 13
FEATURE                 Location/Qualifiers
misc_feature            1..13
                        note = Synthetic: Cr-B
modified_base           1
                        mod_base = OTHER
                        note = 5'-phosphate
source                  1..13
                        mol_type = other DNA
                        organism = synthetic construct
SEQUENCE: 18
cactggcatc tgg                                                       13

SEQ ID NO: 19           moltype = DNA  length = 10
FEATURE                 Location/Qualifiers
misc_feature            1..10
                        note = Synthetic: Cr-C
modified_base           1
                        mod_base = OTHER
                        note = 5'-phosphate
source                  1..10
                        mol_type = other DNA
                        organism = synthetic construct
SEQUENCE: 19
cgcaggtgtt                                                           10

SEQ ID NO: 20           moltype = DNA  length = 13
FEATURE                 Location/Qualifiers
misc_feature            1..13
                        note = Synthetic: Cr-D
modified_base           1
                        mod_base = OTHER
                        note = 5'-phosphate
source                  1..13
                        mol_type = other DNA
                        organism = synthetic construct
SEQUENCE: 20
gtaaggagct gct                                                       13

SEQ ID NO: 21           moltype = DNA  length = 1600
FEATURE                 Location/Qualifiers
misc_feature            1..1600
                        note = Synthetic: TRAC genomic sequence
source                  1..1600
                        mol_type = other DNA
                        organism = synthetic construct
SEQUENCE: 21
```

```
ggctccaact aacatttgtt tggtacttta cagtttatta aatagatgtt tatatggaga    60
agctctcatt tctttctcag aagagcctgg ctaggaaggt ggatgaggca ccatattcat   120
tttgcaggtg aaattcctga gatgtaagga gctgctgtga cttgctcaag gccttatatc   180
gagtaaacgg tagtgctggg cttagacgc aggtgttctg atttatagtt caaaacctct   240
atcaatgaga gagcaatctc ctggtaatgt gatagattc ccaacttaat gccaacatac   300
cataaacctc ccattctgct aatgcccagc ctaagttggg gagaccactc cagattccaa   360
gatgtacagt ttgctttgct gggccttttt cccatgcctg cctttactct gccagagtta   420
tattgctggg gttttgaaga agatcctatt aaataaaaga ataagcagta ttattaagta   480
gccctgcatt tcaggtttcc ttgagtggca ggccaggcct ggccgtgaac gttcactgaa   540
atcatggcct cttggccaag attgatagct tgtgcctgtc cctgagtccc agtccatcac   600
gagcagctgg tttctaagat gctatttccc gtataaagca tgagaccgtg acttgccagc   660
cccacagagc cccgcccttg tccatcactg gcatctggac tccagcctgg gttgggcaa    720
agagggaaat gagatcatgt cctaaccctg atcctcttgt cccacagata tccagaaccc   780
tgaccctgcc gtgtaccagc tgagagactc taaatccagt gacaagtctg tctgcctatt   840
caccgatttt gattctcaaa caaatgtgtc acaaagtaag gattctgatg tgtatatcac   900
agacaaaact gtgctagaca tgaggtctat ggacttcaag agcaacagtg ctgtggcctg   960
gagcaacaaa tctgactttg catgtgcaaa cgccttcaac aacagcatta ttccagaaga  1020
caccttcttc cccagcccag gtaagggcag ctttggtgcc ttcgcaggct gtttccttgc  1080
ttcaggaatg gccaggttct gcccagagct ctggtcaatg atgtctaaaa ctcctctgat  1140
tggtggtctc ggccttatcc attgccacca aaacccctctt tttactaaga aacagtgagc  1200
cttgttctgg cagtccagag aatgacacgg gaaaaaagca gatgaagaga aggtggcagg  1260
agagggcacg tgggccagcc tcagtctctc caactgaggct cctgcctgcc tgcctttgct  1320
cagactgttt gccccttact gctcttctag gcctcattct aagccccttc tccaagttgc  1380
ctctccttat ttctccctgt ctgccaaaaa atctttccca gctcactaag tcagtctcac  1440
gcagtcactc attaacccac caatcactga ttgtgccggc acatgaatgc accaggtgtt  1500
gaagtggagg aattaaaaag tcagatgagg ggtgtgccca gaggaagcac cattctagtt  1560
gggggagccc atctgtcagc tgggaaaagt ccaataact                         1600

SEQ ID NO: 22             moltype = DNA   length = 54
FEATURE                   Location/Qualifiers
source                    1..54
                          mol_type = other DNA
                          organism = synthetic construct
SEQUENCE: 22
catgtattca ttatatctgg tgagtcatcc caggtggcac cacgtgcaac ccca                54

SEQ ID NO: 23             moltype = DNA   length = 31
FEATURE                   Location/Qualifiers
source                    1..31
                          mol_type = other DNA
                          organism = synthetic construct
SEQUENCE: 23
catgtattca ttatatctgg tgagtcatcc c                                          31

SEQ ID NO: 24             moltype = DNA   length = 31
FEATURE                   Location/Qualifiers
source                    1..31
                          mol_type = other DNA
                          organism = synthetic construct
modified_base             1
                          mod_base = OTHER
                          note = 5'-phosphate
SEQUENCE: 24
gggatgactc accagatata atgaatacat g                                          31

SEQ ID NO: 25             moltype = DNA   length = 23
FEATURE                   Location/Qualifiers
source                    1..23
                          mol_type = other DNA
                          organism = synthetic construct
modified_base             1
                          mod_base = OTHER
                          note = 5'-phosphate
SEQUENCE: 25
aggtggcacc acgtgcaacc cca                                                   23

SEQ ID NO: 26             moltype = DNA   length = 17
FEATURE                   Location/Qualifiers
source                    1..17
                          mol_type = other DNA
                          organism = synthetic construct
SEQUENCE: 26
tggggttgca cgtggtg                                                          17

SEQ ID NO: 27             moltype = DNA   length = 28
FEATURE                   Location/Qualifiers
source                    1..28
                          mol_type = other DNA
                          organism = synthetic construct
```

| | |
|---|---|
| misc_difference | 1..5 |
| | note = a, c, t, g, unknown or other |

SEQUENCE: 27 nnnnnaggtg gcaccacgtg caacccca          28